(12) United States Patent
Voronenko et al.

(10) Patent No.: US 11,801,398 B2
(45) Date of Patent: Oct. 31, 2023

(54) BEAM STATION TREATMENT PLANNING AND RADIATION DELIVERY METHODS

(71) Applicant: RefleXion Medical, Inc., Hayward, CA (US)

(72) Inventors: Yevgen Voronenko, San Jose, CA (US); Jayakrishnan Janardhanan, Union City, CA (US); Debashish Pal, Sunnyvale, CA (US); Rostem Bassalow, Lacey, WA (US); Peter Demetri Olcott, Los Gatos, CA (US); Michael Kirk Owens, North Easton, MA (US)

(73) Assignee: RefleXion Medical, Inc., Hayward, CA (US)

( * ) Notice: Subject to any disclaimer, the term of this patent is extended or adjusted under 35 U.S.C. 154(b) by 0 days.

(21) Appl. No.: 17/831,105

(22) Filed: Jun. 2, 2022

(65) Prior Publication Data
US 2022/0288422 A1 Sep. 15, 2022

Related U.S. Application Data

(63) Continuation of application No. 16/274,962, filed on Feb. 13, 2019, now Pat. No. 11,358,008.
(Continued)

(51) Int. Cl.
*A61N 5/10* (2006.01)
*A61B 6/00* (2006.01)
(Continued)

(52) U.S. Cl.
CPC ............ *A61N 5/1079* (2013.01); *A61B 6/035* (2013.01); *A61B 6/037* (2013.01); *A61B 6/0407* (2013.01);
(Continued)

(58) Field of Classification Search
CPC .... A61N 5/1079; A61N 5/103; A61N 5/1045; A61N 5/1049; A61N 5/107;
(Continued)

(56) References Cited

U.S. PATENT DOCUMENTS 3,794,840 A 2/1974 Scott
4,771,785 A 9/1988 Duer
(Continued)

FOREIGN PATENT DOCUMENTS

CN 1681436 A 10/2005
CN 1960780 A 5/2007
(Continued)

OTHER PUBLICATIONS

AAPM (2012). Planning evaluation of step-and-shoot IMRT, RapidArc™, and helical tomotherapy for hippocampal-avoidance whole brain radiotherapy (HA-WBRT), 2 total pages.
(Continued)

*Primary Examiner* — Peter Luong
(74) *Attorney, Agent, or Firm* — Cooley LLP

(57) ABSTRACT

Described herein are methods for beam station delivery of radiation treatment, where the patient platform is moved to a series of discrete patient platform locations or beam stations that are determined during treatment planning, stopped at each of these locations while the radiation source rotates about the patient delivering radiation to the target regions that intersect the radiation beam path, and then moving to the next location after the prescribed dose of radiation (e.g., in accordance with a calculated fluence map) for that location has been delivered to the patient.

23 Claims, 6 Drawing Sheets

Related U.S. Application Data

(60) Provisional application No. 62/629,881, filed on Feb. 13, 2018.

(51) Int. Cl.
*A61B 6/03* (2006.01)
*A61B 6/04* (2006.01)

(52) U.S. Cl.
CPC .............. *A61B 6/4435* (2013.01); *A61B 6/54* (2013.01); *A61N 5/103* (2013.01); *A61N 5/107* (2013.01); *A61N 5/1045* (2013.01); *A61N 5/1049* (2013.01); *A61N 5/1071* (2013.01); *A61N 5/1075* (2013.01); *A61N 5/1081* (2013.01); *A61N 5/1068* (2013.01); *A61N 2005/1052* (2013.01); *A61N 2005/1055* (2013.01); *A61N 2005/1058* (2013.01); *A61N 2005/1061* (2013.01); *A61N 2005/1072* (2013.01)

(58) Field of Classification Search
CPC .. A61N 5/1071; A61N 5/1075; A61N 5/1081; A61N 5/1068; A61N 2005/1052; A61N 2005/1055; A61N 2005/1058; A61N 2005/1061; A61N 2005/1072; A61B 6/035; A61B 6/037; A61B 6/0407; A61B 6/4435; A61B 6/54; A61B 6/032
See application file for complete search history.

(56) References Cited

U.S. PATENT DOCUMENTS

| | | |
|---|---|---|
| 5,262,649 A | 11/1993 | Antonuk et al. |
| 5,394,452 A | 2/1995 | Swerdloff et al. |
| 5,418,827 A | 5/1995 | Deasy et al. |
| 5,511,549 A | 4/1996 | Legg et al. |
| 5,548,627 A | 8/1996 | Swerdloff et al. |
| 5,647,663 A | 7/1997 | Holmes |
| 5,661,773 A | 8/1997 | Swerdloff et al. |
| 5,724,400 A | 3/1998 | Swerdloff et al. |
| 5,813,985 A | 9/1998 | Carroll |
| 6,023,494 A | 2/2000 | Senzig et al. |
| 6,038,283 A | 3/2000 | Carol et al. |
| 6,094,760 A | 8/2000 | Nonaka et al. |
| 6,393,096 B1 | 5/2002 | Carol et al. |
| 6,455,856 B1 | 9/2002 | Gagnon |
| 6,459,762 B1 | 10/2002 | Wong et al. |
| 6,459,769 B1 | 10/2002 | Cosman |
| 6,504,899 B2 | 1/2003 | Pugachev et al. |
| 6,661,870 B2 | 12/2003 | Kapatoes et al. |
| 6,700,949 B2 | 3/2004 | Susami et al. |
| 6,714,620 B2 | 3/2004 | Caflisch et al. |
| 6,735,277 B2 | 5/2004 | McNutt et al. |
| 7,015,490 B2 | 3/2006 | Wang et al. |
| 7,110,808 B2 | 9/2006 | Adair |
| 7,227,925 B1 | 6/2007 | Mansfield et al. |
| 7,265,356 B2 | 9/2007 | Pelizzari et al. |
| 7,266,175 B1 | 9/2007 | Romesberg |
| 7,302,038 B2 | 11/2007 | Mackie et al. |
| 7,343,030 B2 | 3/2008 | Sawyer |
| 7,453,983 B2 | 11/2008 | Schildkraut et al. |
| 7,453,984 B2 | 11/2008 | Chen et al. |
| 7,496,181 B2 | 2/2009 | Mazin et al. |
| 7,508,967 B2 | 3/2009 | Harari et al. |
| 7,513,861 B2 | 4/2009 | Klein et al. |
| 7,611,452 B2 | 11/2009 | Allison et al. |
| 7,639,853 B2 | 12/2009 | Olivera et al. |
| 7,657,304 B2 | 2/2010 | Mansfield et al. |
| 7,693,257 B2 | 4/2010 | Allison |
| 7,715,606 B2 | 5/2010 | Jeung et al. |
| 7,831,073 B2 | 11/2010 | Fu et al. |
| 7,839,972 B2 | 11/2010 | Ruchala et al. |
| 7,885,371 B2 | 2/2011 | Thibault et al. |
| 7,949,095 B2 | 5/2011 | Ning et al. |
| 7,983,380 B2 | 7/2011 | Guertin et al. |
| 8,017,915 B2 | 9/2011 | Mazin |
| 8,019,042 B2 | 9/2011 | Shukla et al. |
| 8,063,376 B2 | 11/2011 | Maniawski et al. |
| 8,090,074 B2 | 1/2012 | Filiberti et al. |
| 8,144,962 B2 | 3/2012 | Busch et al. |
| 8,148,695 B2 | 4/2012 | Takahashi et al. |
| 8,149,991 B2 | 4/2012 | More |
| 8,160,205 B2 | 4/2012 | Saracen et al. |
| 8,232,535 B2 | 7/2012 | Olivera et al. |
| 8,260,013 B2 | 9/2012 | Pekar et al. |
| 8,280,002 B2 | 10/2012 | Bani-Hashemi et al. |
| 8,295,906 B2 | 10/2012 | Saunders et al. |
| 8,406,844 B2 | 3/2013 | Ruchala et al. |
| 8,461,538 B2 | 6/2013 | Mazin |
| 8,467,497 B2 | 6/2013 | Lu et al. |
| 8,483,357 B2 | 7/2013 | Siljamaki et al. |
| 8,509,383 B2 | 8/2013 | Lu et al. |
| 8,588,367 B2 | 11/2013 | Busch et al. |
| 8,606,349 B2 | 12/2013 | Rousso et al. |
| 8,716,669 B2 | 5/2014 | Myaoka et al. |
| 8,745,789 B2 | 6/2014 | Saracen et al. |
| 8,748,825 B2 | 6/2014 | Mazin |
| 8,767,917 B2 | 7/2014 | Ruchala et al. |
| 8,841,628 B2 | 9/2014 | Kitano et al. |
| 9,061,141 B2 | 6/2015 | Brunker et al. |
| 9,155,909 B2 | 10/2015 | Ishikawa |
| 9,205,281 B2 | 12/2015 | Mazin |
| 9,456,764 B2 | 10/2016 | Burke et al. |
| 9,731,148 B2 | 8/2017 | Olivera et al. |
| 9,820,700 B2 | 11/2017 | Mazin |
| 10,327,716 B2 | 6/2019 | Mazin |
| 10,406,382 B2 | 9/2019 | Humber et al. |
| 10,617,888 B2 | 4/2020 | Pal et al. |
| 10,695,586 B2 | 6/2020 | Harper et al. |
| 10,702,715 B2 | 7/2020 | Pearce et al. |
| 10,745,253 B2 | 8/2020 | Saracen et al. |
| 10,912,950 B2 | 2/2021 | Pal et al. |
| 10,918,884 B2 | 2/2021 | O'Connor et al. |
| 10,959,686 B2 | 3/2021 | Mazin |
| 11,309,072 B2 | 4/2022 | Carmi |
| 11,358,008 B2 | 6/2022 | Voronenko et al. |
| 2002/0191734 A1 | 12/2002 | Kohima et al. |
| 2002/0193685 A1 | 12/2002 | Mate et al. |
| 2003/0036700 A1 | 2/2003 | Weinberg |
| 2003/0128801 A1 | 7/2003 | Eisenberg et al. |
| 2003/0219098 A1 | 11/2003 | McNutt et al. |
| 2004/0024300 A1 | 2/2004 | Graf |
| 2004/0030246 A1 | 2/2004 | Townsend et al. |
| 2004/0037390 A1 | 2/2004 | Mihara et al. |
| 2004/0057557 A1 | 3/2004 | Nafstadius |
| 2004/0096033 A1 | 5/2004 | Seppi et al. |
| 2004/0120452 A1 | 6/2004 | Shapiro et al. |
| 2004/0158416 A1 | 8/2004 | Slates |
| 2004/0162457 A1 | 8/2004 | Maggiore et al. |
| 2004/0184579 A1 | 9/2004 | Mihara et al. |
| 2004/0264640 A1 | 12/2004 | Myles |
| 2005/0028279 A1 | 2/2005 | de Mooy |
| 2005/0089135 A1 | 4/2005 | Toth et al. |
| 2005/0109939 A1 | 5/2005 | Engler et al. |
| 2005/0111621 A1 | 5/2005 | Riker et al. |
| 2005/0111757 A1 | 5/2005 | Brackett et al. |
| 2005/0113961 A1 | 5/2005 | Sabol et al. |
| 2005/0197564 A1 | 9/2005 | Dempsey |
| 2006/0002511 A1 | 1/2006 | Miller et al. |
| 2006/0058637 A1 | 3/2006 | Sommer |
| 2006/0072699 A1 | 4/2006 | Mackie et al. |
| 2006/0113482 A1 | 6/2006 | Pelizzari et al. |
| 2006/0173294 A1 | 8/2006 | Ein-Gal |
| 2006/0182326 A1 | 8/2006 | Schildkraut et al. |
| 2006/0193435 A1 | 8/2006 | Hara et al. |
| 2006/0237652 A1 | 10/2006 | Kimchy et al. |
| 2006/0241332 A1 | 10/2006 | Klein et al. |
| 2006/0293583 A1 | 12/2006 | Saracen et al. |
| 2007/0003010 A1 | 1/2007 | Guertin et al. |
| 2007/0003123 A1 | 1/2007 | Fu et al. |
| 2007/0014391 A1 | 1/2007 | Mostafavi et al. |
| 2007/0041500 A1* | 2/2007 | Olivera ................ A61N 5/1042 378/65 |

(56) References Cited

U.S. PATENT DOCUMENTS

| | | |
|---|---|---|
| 2007/0043289 A1 | 2/2007 | Adair |
| 2007/0055144 A1 | 3/2007 | Neustadter et al. |
| 2007/0075273 A1 | 4/2007 | Birgy et al. |
| 2007/0133749 A1 | 6/2007 | Mazin et al. |
| 2007/0211857 A1 | 9/2007 | Urano et al. |
| 2007/0221869 A1 | 9/2007 | Song |
| 2007/0242801 A1 | 10/2007 | Mackie et al. |
| 2007/0265528 A1 | 11/2007 | Xu et al. |
| 2008/0002811 A1 | 1/2008 | Allison |
| 2008/0031406 A1 | 2/2008 | Yan et al. |
| 2008/0071131 A1 | 3/2008 | Rietzel |
| 2008/0128631 A1 | 6/2008 | Suhami |
| 2008/0130825 A1 | 6/2008 | Fu et al. |
| 2008/0152085 A1 | 6/2008 | Saracen et al. |
| 2008/0156993 A1 | 7/2008 | Weinberg et al. |
| 2008/0205588 A1 | 8/2008 | Kim |
| 2008/0230705 A1 | 9/2008 | Rousso et al. |
| 2008/0235873 A1 | 10/2008 | Farooqui |
| 2008/0253516 A1 | 10/2008 | Hui et al. |
| 2008/0273659 A1 | 11/2008 | Guertin et al. |
| 2008/0298536 A1 | 12/2008 | Ein-Gal |
| 2009/0086909 A1 | 4/2009 | Hui et al. |
| 2009/0116616 A1 | 5/2009 | Lu et al. |
| 2009/0169082 A1 | 7/2009 | Mizuta et al. |
| 2009/0296886 A1 | 12/2009 | Maltz et al. |
| 2009/0309046 A1 | 12/2009 | Balakin |
| 2010/0049030 A1 | 2/2010 | Saunders et al. |
| 2010/0054412 A1 | 3/2010 | Brinks et al. |
| 2010/0069742 A1 | 3/2010 | Partain et al. |
| 2010/0074400 A1 | 3/2010 | Sendai |
| 2010/0074498 A1 | 3/2010 | Breeding et al. |
| 2010/0176309 A1 | 7/2010 | Mackie et al. |
| 2010/0198063 A1 | 8/2010 | Huber et al. |
| 2010/0220832 A1 | 9/2010 | Ning et al. |
| 2010/0237259 A1 | 9/2010 | Wang |
| 2011/0057122 A1 | 3/2011 | Moyers |
| 2011/0073763 A1 | 3/2011 | Subbarao |
| 2011/0092814 A1 | 4/2011 | Yamaya et al. |
| 2011/0215259 A1 | 9/2011 | Iwata |
| 2011/0301449 A1 | 12/2011 | Maurer, Jr. |
| 2012/0020449 A1 | 1/2012 | Yan et al. |
| 2012/0043481 A1 | 2/2012 | Mansfield et al. |
| 2012/0053961 A1 | 3/2012 | Wang et al. |
| 2012/0138804 A1 | 6/2012 | Miyaoka et al. |
| 2012/0161014 A1 | 6/2012 | Yamaya et al. |
| 2012/0230464 A1 | 9/2012 | Ling et al. |
| 2012/0292534 A1 | 11/2012 | Geneser et al. |
| 2013/0111668 A1 | 5/2013 | Wiggers et al. |
| 2013/0336449 A1 | 12/2013 | Tanabe |
| 2014/0005464 A1 | 1/2014 | Bharat et al. |
| 2014/0105355 A1 | 4/2014 | Toimela et al. |
| 2014/0126700 A1 | 5/2014 | Gertner et al. |
| 2014/0275697 A1 | 9/2014 | Filiberti |
| 2014/0321615 A1 | 10/2014 | Carlsson |
| 2014/0348297 A1 | 11/2014 | Burshtein et al. |
| 2016/0023019 A1 | 1/2016 | Filiberti et al. |
| 2016/0045173 A1 | 2/2016 | Bailey et al. |
| 2016/0331997 A1 | 11/2016 | Vilsmeier |
| 2017/0023494 A1 | 1/2017 | Yu et al. |
| 2017/0028221 A1 | 2/2017 | Kontaxis et al. |
| 2017/0084025 A1 | 3/2017 | Lyu |
| 2017/0209715 A1 | 7/2017 | Ruebel et al. |
| 2018/0110483 A1 | 4/2018 | Mazin |
| 2018/0133508 A1 | 5/2018 | Pearce et al. |
| 2018/0133518 A1 | 5/2018 | Harper et al. |
| 2019/0001152 A1 | 1/2019 | O'Connor et al. |
| 2019/0091487 A1 | 3/2019 | Pal et al. |
| 2019/0255362 A1 | 8/2019 | Voronenko et al. |
| 2020/0368551 A1 | 11/2020 | Bassalow et al. |
| 2021/0196212 A1 | 7/2021 | Mazin |
| 2023/0067048 A1 | 3/2023 | Voronenko et al. |

FOREIGN PATENT DOCUMENTS

| | | |
|---|---|---|
| CN | 101267767 A | 9/2008 |
| CN | 102160913 A | 8/2011 |
| CN | 103006253 A | 4/2013 |
| CN | 103126713 A | 6/2013 |
| CN | 103517737 A | 1/2014 |
| CN | 104866928 A | 8/2015 |
| CN | 104994909 A | 10/2015 |
| EP | 0 212 135 B1 | 9/1991 |
| EP | 1 454 653 B1 | 9/2007 |
| EP | 1 402 761 B1 | 8/2008 |
| EP | 1 660 175 B1 | 2/2012 |
| EP | 2 777 768 A1 | 9/2014 |
| EP | 3 175 886 B1 | 6/2018 |
| JP | 2905995 B2 | 6/1999 |
| JP | H-11-313900 A | 11/1999 |
| JP | 2000-342639 A | 12/2000 |
| JP | 2002-522128 A | 7/2002 |
| JP | 2006-007464 A | 1/2006 |
| JP | 2007-502166 A | 2/2007 |
| JP | 2007-507246 A | 3/2007 |
| JP | 2007-083036 A | 4/2007 |
| JP | 2008-237911 A | 10/2008 |
| JP | 2009-502249 A | 1/2009 |
| JP | 2011-528977 A | 12/2011 |
| JP | 2012-506748 A | 3/2012 |
| JP | 2014-061445 A | 4/2014 |
| JP | 2015-231497 A | 12/2015 |
| JP | 2016-174674 A | 10/2016 |
| WO | WO-94/28971 A2 | 12/1994 |
| WO | WO-94/28971 A3 | 12/1994 |
| WO | WO-03/018132 A1 | 3/2003 |
| WO | WO-03/076003 A2 | 9/2003 |
| WO | WO-03/076003 A3 | 9/2003 |
| WO | WO-2004/017832 A2 | 3/2004 |
| WO | WO-2004/017832 A3 | 3/2004 |
| WO | WO-2004/105574 A2 | 12/2004 |
| WO | WO-2004/105574 A3 | 12/2004 |
| WO | WO-2005/018734 A2 | 3/2005 |
| WO | WO-2005/018734 A3 | 3/2005 |
| WO | WO-2005/018735 A2 | 3/2005 |
| WO | WO-2005/018735 A3 | 3/2005 |
| WO | WO-2005/031629 A1 | 4/2005 |
| WO | WO-2005/110495 A1 | 11/2005 |
| WO | WO-2007/082126 A2 | 7/2007 |
| WO | WO-2007/082126 A3 | 7/2007 |
| WO | WO-2007/124760 A1 | 11/2007 |
| WO | WO-2008/011725 A1 | 1/2008 |
| WO | WO-2008/024463 A2 | 2/2008 |
| WO | WO-2008/024463 A3 | 2/2008 |
| WO | WO-2015/168431 A1 | 11/2015 |
| WO | WO-2016/061877 A1 | 4/2016 |
| WO | WO-2016/064750 A1 | 4/2016 |
| WO | WO-2017/048852 A1 | 3/2017 |
| WO | WO-2017/156316 A1 | 9/2017 |
| WO | WO-2018/093933 A1 | 5/2018 |
| WO | WO-2018/222751 A1 | 12/2018 |
| WO | WO-2019/060764 A1 | 3/2019 |

OTHER PUBLICATIONS

Abstract ID: 3577 Title: Dosimetric comparison of helical TomoTherapy treatment and step-and-shoot intensity-modulated radiotherapy treatment on stereotactic radiosurgery, 2006, 1 total page.

Bangert, M. et al. (2016). "Accelerated iterative beam angle selection in IMRT," Medical Physics 43.3:1073-1082.

Best Nomos (2008). NomosSTAT Serial Tomotherapy Brochure, 6 total pages.

Chang, S.X. et al. (2000). "Intensity modulation delivery techniques: "Step & Shoot" MLC auto-sequence versus the use of a modulator," Med. Phys. 27:948-959.

Chen, X. et al. (2012). "Smoothing proximal gradient method for general structured sparse regression," The Annals of Applied Statistics 6:719-752.

Corrected Notice of Allowability dated Feb. 3, 2021, for U.S. Appl. No. 16/425,416, filed May 29, 2019, 2 pages.

(56) References Cited

OTHER PUBLICATIONS

Corrected Notice of Allowability dated Mar. 16, 2023, for U.S. Appl. No. 17/203,532, filed Mar. 16, 2021, 2 pages.
Dieterich, S. et al. (2003). "Skin respiratory motion tracking for stereotactic radiosurgery using the CyberKnife," *Elsevier Int'l Congress Series* 1256:130-136.
Elekta Oncology (2008). "HexaPOD™ evo RT System Brochure," 8 total pages.
Erdi, Y.E. (Feb. 2007). "The Use of PET for Radiotherapy," *Current Medical Imaging Reviews* 3(1):3-16.
Extended European Search Report dated Mar. 31, 2017, for European Application No. 09 719 473.2, filed on Mar. 9, 2009, 8 pages.
Extended European Search Report dated Oct. 15, 2019, for European Application No. 17 764 132.1, filed on Mar. 9, 2017, 4 pages.
Extended European Search Report dated Sep. 2, 2020, for European Application No. 17 871 896.1, filed on Nov. 15, 2017, 9 pages.
Extended European Search Report dated May 19, 2021, for European Application No. 18 857 863.7, filed on Sep. 21, 2018, 7 pages.
Extended European Search Report dated Oct. 15, 2021, for European Application No. 19 754 923.1, filed on Feb. 13, 2019, 11 pages.
Fan, Q. (Nov. 2012). "Emission Guided Radiation Therapy for Lung and Prostrate Cancers: A Feasibility Study on a Digital Patient," *Med. Phys.* 39(11):7140-7152.
Fan, Q. et al. (Aug. 2013). "Toward a Planning Scheme for Emission Guided Radiation Therapy (EGRT): FDG Based Tumor Tracking in a Metastatic Breast Cancer Patient," *Med. Phys.* 40(8):081708, 12 pages.
Final Office Action dated Aug. 15, 2012, for U.S. Appl. No. 13/209,275, filed Aug. 12, 2011, 8 pages.
Gibbons, J.P. (2004). "Dose calculation and verification for tomotherapy," 2004 ACMP Meeting, Scottsdale, AZ., 71 total pages.
Handsfield, L.L. et al. (2014). "Phantomless patient-specific TomoTherapy QA via delivery performance monitoring and a secondary Monte Carlo dose calculation," *Med. Phys.* 41:101703-1-101703-9.
Hunt, M.A. et al. (2003). "Treatment Planning Considerations using IMRT," pp. 103-121.
Internal Atomic Energy Agency (Oct. 2008). "The Role of PET/CT in Radiation Treatment Planning for Cancer Patient Treatment," located at https://www-pub.iaea.org/MTCD/Publications/PDF/te_1603_web.pdf, 40 total pages.
International Search Report dated May 4, 2009, for PCT Patent Application No. PCT/US2009/01500, filed on Mar. 9, 2009, 3 pages.
International Search Report dated Jun. 27, 2017, for PCT Patent Application No. PCT/US2017/021647, filed on Mar. 9, 2017, 3 pages.
International Search Report dated Mar. 13, 2018, for PCT Application No. PCT/US2017/061855, filed on Nov. 15, 2017, 4 pages.
International Search Report dated Jan. 18, 2019, for PCT Application No. PCT/US2018/052272, filed on Sep. 21, 2018, 4 pages.
International Search Report dated Jun. 14, 2019, for PCT Application No. PCT/US2019/017855, filed on Feb. 13, 2019, 4 pages.
International Search Report dated Apr. 23, 2020, for PCT Application No. PCT/US2020/013927, filed on Jan. 16, 2020, 3 pages.
International Search Report dated Dec. 1, 2020, for PCT Application No. PCT/US2020/040774, filed on Jul. 2, 2020, 4 pages.
Kapatoes, J.M. et al. (2001). "A feasible method for clinical delivery verification and dose reconstruction in tomotherapy," *Med. Phys.* 28:528-542.
Kapatoes, J. M. (2001). "On the accuracy and effectiveness of dose reconstruction for tomotherapy," *Physics in Med. Biol.* 46:943-966.
Keall, P.J. et al. (2001). "Motion adaptive x-ray therapy: a feasibility study," *Physics in Med. Biol.* 46:1-10.
Kim, Y.N. et al. (2013). "A comparative planning study of step-and-shoot IMRT versus helical tomotherapy in a model patient," J. Korean Physical Society 63:1481-1485.
Krouglicof, N. et al. (Nov. 2013). "Development of a Novel PCB-Based Voice Coil Actuator for Opto-Mechatronic Applications," presented at *IEEE/RSJ International Conference on Intelligent Robots and Systems* (*IROS*), Tokyo, Japan, Nov. 3-7, 2013, pp. 5834-5840.
Lee, S. et al. (2015). "Treatment plan comparison of Linac step and shoot, tomotherapy, RapidArc, and proton therapy for prostate cancer using dosimetrical and biological index," J. Korean Physical Society 67:7-16 (with tables 1-5), 28 total pages.
Mackie, T.R. et al. (Nov.-Dec. 1993). "Tomotherapy: A New Concept for the Delivery of Dynamic Conformal Radiotherapy," *Med. Phys.* 20(6):1709-1719.
Manikandan et al. (2013). "Role of step size and max dwell time in anatomy based inverse optimization for prostate implants," J. Med. Phys. 38:148-154.
Mazin, S.R. et al. (Dec. 2010). "Emission-Guided Radiation Therapy: Biologic Targeting and Adaptive Treatment," *Journal of American College of Radiology* 7(12):989-990.
Non-Final Office Action dated Jan. 10, 2011, for U.S. Appl. No. 12/367,679, filed Feb. 9, 2009, 9 pages.
Non-Final Office Action dated Feb. 28, 2012, for U.S. Appl. No. 13/209,275, filed Aug. 12, 2011, 8 pages.
Non-Final Office Action dated Sep. 19, 2013, for U.S. Appl. No. 13/895,255, filed May 15, 2013, 8 pages.
Non-Final Office Action dated Jun. 26, 2020, for U.S. Appl. No. 16/122,735, filed Sep. 5, 2018, 16 pages.
Non-Final Office Action dated Mar. 3, 2022, for U.S. Appl. No. 17/150,977, filed Jan. 15, 2021, 8 pages.
Non-Final Office Action dated Mar. 3, 2022, for U.S. Appl. No. 16/274,962, filed Feb. 13, 2019, 12 pages.
Non-Final Office Action dated Jul. 5, 2022, for U.S. Appl. No. 17/203,532, filed Mar. 16, 2021, 13 pages.
Non-Final Office Action dated Jan. 20, 2023, for U.S. Appl. No. 16/890,194, filed Jun. 2, 2020, 11 pages.
Notice of Allowance dated Jul. 25, 2011, for U.S. Appl. No. 12/367,679, filed Feb. 9, 2009, 7 pages.
Notice of Allowance dated Apr. 9, 2014, for U.S. Appl. No. 13/895,255, filed May 15, 2013, 7 pages.
Notice of Allowance dated Oct. 27, 2015, for U.S. Appl. No. 14/278,973, filed May 15, 2014, 8 pages.
Notice of Allowance dated Mar. 27, 2013, for U.S. Appl. No. 13/209,275, filed Aug. 12, 2011, 9 pages.
Notice of Allowance dated Oct. 5, 2017, for U.S. Appl. No. 14/951,194, filed Nov. 24, 2015, 11 pages.
Notice of Allowance dated Apr. 4, 2019, for U.S. Appl. No. 15/807,383, filed Nov. 8, 2017, 11 pages.
Notice of Allowance dated Jan. 21, 2020, for U.S. Appl. No. 16/138,631, filed Sep. 21, 2018, 11 pages.
Notice of Allowance dated Apr. 3, 2020, for U.S. Appl. No. 15/814,276, filed Nov. 15, 2017, 10 pages.
Notice of Allowance dated Nov. 19, 2020, for U.S. Appl. No. 16/814,867, filed Mar. 10, 2020, 10 pages.
Notice of Allowance dated Dec. 11, 2020, for U.S. Appl. No. 16/122,735, filed Sep. 5, 2018, 10 pages.
Notice of Allowance dated Jan. 12, 2021, for U.S. Appl. No. 16/425,416, filed May 29, 2019, 13 pages.
Notice of Allowance dated Apr. 12, 2022, for U.S. Appl. No. 16/274,962, filed Feb. 13, 2019, 8 pages.
Notice of Allowance dated Jun. 15, 2022, for U.S. Appl. No. 17/150,977, filed Jan. 15, 2021, 8 pages.
Notice of Allowance dated Dec. 15, 2022, for U.S. Appl. No. 17/203,532, filed Mar. 16, 2021, 8 pages.
Papanikolaou, N. et al. (2010). "MU-Tomo: Independent dose validation software for helical tomo therapy," *J. Cancer Sci. Ther.* 2:145-152.
Partial Supplementary European Search Report dated Jun. 2, 2020, for European Application No. 17 871 896.1, filed on Nov. 15, 2017, 11 pages.
Petersson, K. et al. (2011). "Conversion of helical tomotherapy plans to step-and-shoot IMRT plans—Pareto front evaluation of plans from a new treatment planning system," Med. Phys. 38:3130-3138.
Prabhaker, R. et al. (2007, e-published Jan. 2008). "An Insight into PET-CT Based Radiotherapy Treatment Planning," *Cancer Therapy* (5):519-524.

(56) References Cited

OTHER PUBLICATIONS

Salter, B.J. (2001). "NOMOS Peacock IMRT utilizing the Beak post collimation device," Med. Dosim. 26:37-45.

Shalchian, B. et al. (2009). "Assessment of the Wavelet Transform in Reduction of Noise from Simulated PET Images," Journal of Nuclear Medicine Technology 37:223-228.

Tashima, H. et al. (Jul. 21, 2012). "A Single-Ring OpenPET Enabling PET Imaging During Radiotherapy," *Phys. Med. Biol.* 57(14):4705-4718.

Varian Medical Systems (2004). "Dynamic Targeting™ Image-Guided Radiation Therapy—A Revolution in Cancer Care," *Business Briefing: US Oncology Review*, Abstract only, 2 pages.

Written Opinion dated May 4, 2009, for PCT Patent Application No. PCT/US2009/01500, filed on Mar. 9, 2009, 5 pages.

Written Opinion of the International Searching Authority dated Jun. 27, 2017, for PCT Patent Application No. PCT/US2017/021647, filed on Mar. 9, 2017, 5 pages.

Written Opinion of the International Searching Authority dated Mar. 13, 2018, for PCT Application No. PCT/US2017/061855, filed on Nov. 15, 2017, 6 pages.

Written Opinion of the International Searching Authority dated Jan. 18, 2019, for PCT Application No. PCT/US2018/052272, filed on Sep. 21, 2018, 14 pages.

Written Opinion of the International Searching Authority dated Jun. 14, 2019, for PCT Application No. PCT/US2019/017855, filed on Feb. 13, 2019, 10 pages.

Written Opinion of the International Searching Authority dated Apr. 23, 2020, for PCT Application No. PCT/US2020/013927, filed on Jan. 16, 2020, 4 pages.

Written Opinion of the International Searching Authority dated Dec. 1, 2020, for PCT Application No. PCT/US2020/040774, filed on Jul. 2, 2020, 8 pages.

Yamaya, T. et al. (Jan. 14, 2008). "A Proposal of an Open PET Geometry," *Physics in Medicine and Biology* 53:757-773.

Yan, D. et al. (1997). "Adaptive radiation therapy," *Physics Med. Biol.* 42:123-132.

Zu'an, Z. et al. (2008). "Study on evaluation model of correlation between irradiation field accuracy and sinking of bed board due to gravity," Chin. J. Radiol. Health Deo. 17:484-486, 11 total pages (with English Translation).

\* cited by examiner

BEAM STATION TREATMENT PLANNING AND RADIATION DELIVERY METHODS

CROSS-REFERENCE TO RELATED APPLICATIONS

This application is a continuation of U.S. application Ser. No. 16/274,962, filed Feb. 13, 2019, which claims priority to U.S. Provisional Patent Application No. 62/629,881, filed Feb. 13, 2018, all of which are hereby incorporated by reference in their entirety.

BACKGROUND

Radiation therapy is a choreographed procedure that requires an extensive treatment planning phase in order to determine an efficient way to deliver the prescribed radiation dose to the target regions in the patient (e.g., tumor regions) while avoiding radiation-sensitive organs and/or structures (e.g., organs-at-risk or OARs). A treatment planning system integrates patient information (e.g., the size, shape, and location of target regions and OARs) along with radiation treatment system machine parameters (e.g., therapeutic radiation source beam generation capabilities and range of motion relative to the patient, configuration of the beam-shaping components, degrees-of-freedom and motion of the patient platform, etc.) to generate a fluence map that includes a set of beamlets that provide the prescribed dose to the target region. The fluence map is then segmented into a series of machine instructions that are executed by the radiation therapy system, with the assumption that once the set of instructions has been fully executed, the prescribed dose objectives have been met.

In an effort to expedite radiation delivery and shorten the duration of a treatment session, a radiation therapy system may have a continuously-moving patient platform as well as a continuously moving radiation source. For example, in helical tomotherapy, therapeutic radiation is delivered to the patient from a radiation source that rotates around the patient while the patient is continuously moving through the plane of the therapeutic beam. In this fashion, patient target regions can move through the treatment beam without pausing.

However, due to the continuous motion of the patient platform, it can be difficult to apply any radiation doses that are missed due to radiation therapy system failures (e.g., collimator malfunction, random magnetron arcs, etc.) or unexpected patient and/or target region motion, since the patient platform would have moved the target region past the treatment beam plane and the exact location of the target region with respect to the therapeutic radiation source may be difficult to precisely determine. This may cause insufficient dose to be delivered at certain target regions. In addition, target regions where increased dose levels are prescribed may not be able to get the full prescribed dose in the time duration in which that target region is within the treatment beam plane. Accordingly, improved methods of radiation delivery (and corresponding methods of treatment planning) are desirable.

BRIEF SUMMARY

Described herein are methods for beam station delivery of radiation treatment, where the patient platform is moved to a series of discrete patient platform locations and/or orientations that are determined during treatment planning, stopped at each of these locations and/or orientations while the radiation source rotates about the patient delivering radiation to the target regions that intersect the radiation beam plane or path, and then moving to the next location and/or orientation after the prescribed dose of radiation (e.g., in accordance with a calculated fluence map) for that location and/or orientation has been delivered to the patient. These discrete platform orientations and/or locations or steps (e.g., along the IEC-Y axis) where therapeutic radiation is delivered while the platform is stopped (i.e., not moving, static) may be called beam stations, and may be defined by the treatment planning system before the treatment session. Beam stations may be specified by coordinates in IEC-X, -Y, and -Z, and/or may be specified by the orientation of the patient platform (e.g., roll, yaw, and pitch of the patient platform). In some variations, the therapeutic radiation source may be mounted on a rotatable gantry, which may continuously move or rotate the therapeutic radiation source during the treatment session, even when the patient platform is stopped at a beam station. The therapeutic radiation source may rotate around or move about the patient platform one or more times while the platform is stopped at a beam station, e.g., two or more times. The gantry may be rotatable through 360° in a single direction (e.g., clockwise or counterclockwise direction) to deliver radiation from firing positions located 360° in-plane about the patient platform or may sweep about the patient platform in arcs of less than 360° in two directions (e.g., alternating between clockwise and counterclockwise directions to deliver radiation from firing positions located along the arcs). A treatment planning system may generate a desired dose distribution profile that corresponds to a prescribed dose of radiation for each target region, define a series of beam stations based on the geometry and location of the target region(s), generate one or more fluence maps for each of the beam stations using dose optimization methods, and may optionally segment the one or more fluence maps for each beam station into machine instructions (e.g., dynamic multi-leaf collimator or MLC leaf configurations, therapeutic radiation source or linac pulse parameters, etc.) for execution by the radiation therapy system during a treatment session.

Beam station radiation delivery may allow for "digital dose delivery", since the radiation therapy system fires at predetermined or specified firing positions and/or patient platform positions and orientations. A fast-spinning gantry (e.g., rotating at about 15 RPM or more, about 50 RPM or more, about 60 RPM or more, about 70 RPM or more) may position the therapeutic radiation source at every firing position multiple times while the patient platform is stationary at a beam station. In such manner, radiation fluence or dose may be delivered in discrete dose quanta over multiple gantry revolutions. In addition, since the patient platform is stationary during radiation delivery, the dose can vary greatly from beam station to beam station (i.e., dose is highly modulated). For example, when the patient platform is at a first beam station, the therapeutic radiation source may deliver radiation over a single gantry revolution (e.g., short dwell time and/or deliver radiation during one of multiple revolutions while delivering little or no radiation during the other revolutions) and when moved to a second beam station, the therapeutic radiation source may deliver a much greater amount of radiation over multiple revolutions (e.g., long dwell time and/or deliver radiation during most or all of the multiple revolutions). Radiation therapy systems with fast-spinning gantries (e.g., rotating at about 15 RPM or more, about 50 RPM or more, about 60 RPM or more, about 70 RPM or more) may be able to deliver radiation over multiple gantry revolutions in a relatively short period of time (e.g., without significantly increasing the treatment time). This range of dose modulation is not available in most helical delivery systems that have constant and/or consistent platform motion, because the platform dwell time at any location along the longitudinal axis of the platform (i.e., IEC-Y axis) remains relatively constant. Sudden increases or decreases in platform speed may be jarring to a patient, and cause unnecessary discomfort, which may result in patient position shifts. Beam station delivery may also mitigate any dose delivery variations due to variations in patient platform motion or speed, since the platform is stationary during the dose delivery. This may help relax the specification (i.e., increase the tolerance) for the platform motion system, and remove platform motion as a factor that affects dose delivery. Beam station radiation delivery methods may also help facilitate gated radiation delivery using radiation therapy system comprising fast-spinning gantries (e.g., rotating at about 15 RPM or more, about 60 RPM or more, about 70 RPM or more) and/or gantries with a large rotational inertia in conjunction with an external breathing sensor.

One variation of a radiation therapy system may comprise a circular gantry rotatable about a longitudinal axis, a therapeutic radiation source mounted on the gantry, a patient platform movable to a plurality of beam stations at predetermined locations along the longitudinal axis, and a controller in communication with the gantry, the radiation source, and the patient platform. The controller may be configured to move the patient platform to a first beam station, stop the patient platform at the first beam station, activate the therapeutic radiation source to emit radiation fluence while the patient platform is at the first beam station, and deactivate the therapeutic radiation source while moving the patient platform from the first beam station to a second beam station. The controller may be configured to stop the patient platform at the second beam station, activate the therapeutic radiation source to emit radiation fluence while the patient platform is at the second beam station, and deactivate the therapeutic radiation source while moving the patient platform from the second beam station to a third beam station. The gantry may be configured to rotate at a speed of about 60 RPM. Some variations may further comprise an imaging system in communication with the controller and configured to acquire imaging data. For example, the imaging system may be a PET imaging system comprising one or more PET detectors configured to detect lines-of-response (LORs) data, and/or a CT imaging system comprising one or more kV radiation detectors configured to acquire CT data. The imaging system may be mounted on the gantry. The controller may be configured to calculate the radiation fluence emitted at the first beam station by using imaging data acquired by the imaging system. In some variations, the controller may be configured to continuously monitor the radiation fluence emitted at the first beam station and to compare the emitted radiation fluence with a planned radiation fluence for the first beam station to calculate a remainder fluence. The controller may be configured to segment the remainder fluence into instructions for the therapeutic radiation source and a dynamic multi-leaf collimator (MLC) disposed in a beam path of the therapeutic radiation source, and to activate the therapeutic radiation source to emit the remainder fluence while the patient platform is stopped at the first beam station. Optionally, the controller may be configured to determine whether the remainder fluence is below a predetermined remainder fluence threshold, and if the remainder fluence is below the remainder fluence threshold, the controller may be configured to deactivate the therapeutic radiation source and move the patient platform to the second beam station. In some variations, the predetermined remainder fluence threshold is zero. The controller may be configured to calculate radiation fluence for emission at the second beam station using imaging data acquired before the therapeutic radiation source is moved to the second beam station. The radiation fluence for emission at the second beam station may be calculated using imaging data acquired while the patient platform was located at the first beam station. Alternatively or additionally, the controller may be configured to segment the radiation fluence for emission at the second beam station into instructions for the therapeutic radiation source and a dynamic multi-leaf collimator (MLC) before radiation is emitted by the therapeutic radiation source at the second beam station. The radiation fluence emitted at the second beam station may be compared to the calculated radiation fluence for emission at the second beam station, and if a difference between the emitted radiation fluence and the calculated radiation fluence is below a predetermined threshold, the controller is configured to move the patient platform from the second beam station to the third beam station.

In some variations, the system controller may be configured to sequentially move the patient platform to each of the plurality of beam stations more than once. For example, the controller may be configured to sequentially move the patient platform to each of the plurality of beam stations in a first direction along the longitudinal axis and to sequentially move the patient platform to each of the plurality of beam stations in a second direction that is opposite the first direction. The radiation fluence emitted at each of the plurality of beam stations while moving the patient platform in the first direction may be different from radiation fluence emitted at each of the plurality of beam stations while moving the patient platform in the second direction. In some variations, the radiation therapy system may further comprise a dynamic multi-leaf collimator (MLC) disposed in a beam path of the therapeutic radiation source, where a configuration of the MLC for the second beam station may be determined according to the calculated radiation fluence for emission at the second beam station. Alternatively or additionally, the controller may be configured to detect one or more malfunctions of one or more of the gantry, therapeutic radiation source, and/or the dynamic MLC during radiation fluence emission, calculate a quantity of radiation fluence that is undelivered because of the one or more detected malfunctions, segment the quantity of undelivered radiation fluence into instructions for the therapeutic radiation source and the dynamic MLC for irradiation, and to activate the therapeutic radiation source to emit the remainder fluence while the patient platform is stopped at the first beam station. The gantry may be configured to rotate at least twice around the patient platform while the patient platform is at each the beam station in the plurality of beam stations. In some variations, each gantry rotation is about 360° around the patient platform.

The controller may be configured to stop the patient platform at each beam station of the plurality of beam stations for a predetermined dwell time. For example, the predetermined dwell time may be from about 5 seconds to about 5 minutes. Alternatively or additionally, each beam station in the plurality of beam stations may be separated by a step distance from about 1 mm to about 2 cm (e.g., about 2.1 mm). The step distance between each beam station of the plurality of beam stations may be the same or different.

One method for calculating a fluence map for beam station radiation delivery may comprise determining a plurality of beam stations based on one or more patient target regions, calculating a set of candidate radiation beamlets for each beam station, and generating a fluence map for each beam station by calculating a set of beamlet weights corresponding to the set of candidate radiation beamlets for each beam station such that radiation dose delivered to the one or more target regions over all candidate radiation beamlets meets pre-determined dose constraints and treatment parameters. The plurality of beam stations may be evenly spaced apart from each other, and may have a beam station pitch or step distance between beam stations of about 2 mm. In some variations, the step distance between each of the beam stations may be variable, or the step distance between each of the beam stations and the number of beam stations in the set of beam station may be user-selected. The set of candidate radiation beamlets may comprise a matrix of multi-leaf collimator (MLC) configurations for each radiation firing position about the patient platform that defines a set of radiation beamlets that intersect the one or more patient target regions. Calculating set of beamlet weights may comprise calculating a dose calculation matrix that comprises the contribution of each candidate beamlet to the one or more target regions. Calculating a set of beamlet weights may comprise generating a penalty function that represents treatment plan quality metrics and using iterative optimization methods to calculate the set of beamlet weights that minimizes the penalty function. The method may also comprise quantizing the fluence map for each beam station to generate a quantized fluence map where each beamlet weight is an integer value of dose quanta deliverable by a movable therapeutic radiation source. In some variations, pre-determined dose constraints may comprise user-defined dose constraints, and/or user-defined dose objectives, and/or maximum dose levels, and/or dose coverage metrics. Treatment parameters may comprise treatment time duration and/or beam station dwell time. The fluence map for each beam station may comprise a l×f matrix, where l is a number of leaves in a multi-leaf collimator in a beam path of a therapeutic radiation source, and f is a number of therapeutic radiation source firing positions around the patient platform. The multi-leaf collimator may be a binary multi-leaf collimator having 64 leaves (e.g., l=64). In some variations, there may be 50 firing stations (e.g., f=50) and/or maybe 100 firing positions (e.g., f=100). In some variations, the method may comprise generating a plurality of fluence maps for each beam station. The plurality of beam stations comprises a plurality of discrete patient platform locations along a longitudinal axis of the patient platform (e.g., along IEC-Y).

One variation of a method for beam station radiation delivery may comprise moving a patient platform to a first beam station of a set of beam stations, delivering radiation to the patient target region in accordance with a first fluence map by moving a therapeutic radiation source about the patient platform while the platform is stationary at the first beam station, and comparing the delivered radiation with the first fluence map and calculating a fluence difference. If the fluence difference does not exceed a predetermined threshold, the method may comprise moving the patient platform to the second beam station of the set of beam stations. If the fluence difference meets or exceeds the predetermined threshold, the method may comprise delivering the fluence difference by continuing to move the therapeutic radiation source about the patient platform before moving the patient platform to the second beam station. The therapeutic radiation source may be mounted on a gantry that is continuously rotatable about the patient platform, and the method may further comprise rotating the gantry multiple revolutions about the patient platform while the patient platform is located at the first beam station. In some variations, the number of revolutions per beam station in the set of beam stations may be from about 5 to about 300, and may vary for each beam station in the set of beam stations, or may be constant for each beam station in the set of beam stations. The patient platform may not remain stationary at a beam station where fluence values of a fluence map for the beam station is zero. In some variations, delivering radiation to the patient target region in accordance with the first fluence map comprises segmenting the first fluence map into multi-leaf collimator configurations for each firing position about the patient platform, and adjusting a multi-leaf collimator disposed in a beam path of the therapeutic radiation source to the multi-leaf collimator configurations at each firing position. A method for beam station radiation delivery may further comprise storing in a memory of a controller a multi-leaf collimator configuration and a firing position for which radiation was not delivered, and moving the therapeutic radiation source to the firing position to re-deliver radiation. In some variations, an adjustable-opening jaw may be disposed in the beam path of the therapeutic radiation source, and delivering radiation may comprise adjusting a width of the jaw opening in accordance with the fluence map. The width of the jaw opening may vary for each beam station in the set of beam stations, or may be constant for each beam station in the set of beam stations. In some variations, the patient target region may move while the patient platform is located at the first beam station, and delivering radiation to the patient target region may comprise directing radiation to the patient target region if it is located within a predetermined treatment location and not directing radiation to the patient target region if it is located outside the predetermined treatment location.

Another variation of a method for beam station radiation delivery may comprise moving a patient platform to a first beam station of a set of beam stations, delivering radiation to the patient target region in accordance with predetermined treatment parameters by moving a therapeutic radiation source about the patient platform while the platform is stationary at the first beam station, and determining whether the delivered radiation complies with the predetermined treatment parameters. If the delivered radiation complies with the predetermined treatment parameters, the method may comprise moving the patient platform to a second beam station of the set of beam stations. If the delivered radiation does not comply with the predetermined treatment parameters, the method may comprise continuing to move the therapeutic radiation source about the patient platform before moving the patient platform to the second beam station. In some variations, the predetermined treatment parameters may comprise one or more dose metrics or one or more radiation delivery instructions. Examples of one or more radiation delivery instructions may comprise at least one of beam station dwell time, jaw opening width, number of therapeutic radiation source revolutions about the patient platform, therapeutic radiation pulse parameters, and/or MLC leaf configurations.

DETAILED DESCRIPTION

Systems

Figure 1:
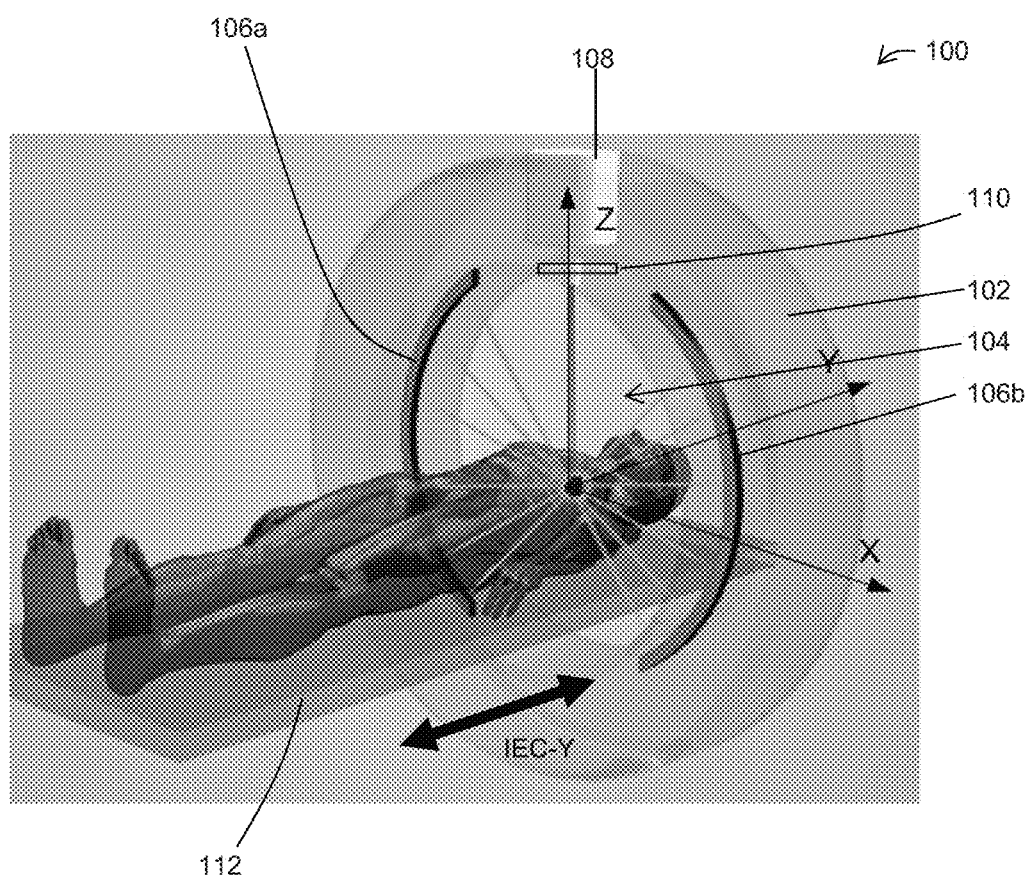
FIG. 1 depicts a schematic representation of one variation of a radiation therapy system.

A radiation therapy system that may be used in beam station radiation delivery may comprise a rotatable gantry that rotates about a patient treatment region, a therapeutic source mounted on the rotatable gantry, and a patient platform movable within or through the patient treatment region. The rotatable gantry may be configured to rotate 0°-360° (e.g., a continuously rotatable gantry) around the patient platform, and/or to only rotate along arc segments that sweep a subset of angles around the patient platform (e.g., 0°-180°, 0°-270°, etc.), and/or to move to a fixed number of angles about the patient platform. For example, the rotatable gantry may be configured to continuously move through each firing position while therapeutic radiation is emitted, or may be configured to step to each firing position where therapeutic radiation is emitted only when the radiation source is stopped at a firing position. In some variations, the gantry may be configured to move to discrete, pre-defined circumferential firing positions or firing angles as it rotates. Some systems have about 50 firing positions or angles (e.g., from about 0° to about 360°, where each firing position is separated by a regular angular interval). Some systems may have about 100 firing positions. Alternatively or additionally, some systems may be configured to have a discrete set of firing positions at arbitrary angles around the patient platform (e.g., at 0°, 45°, 90°, 135°, 180°, etc.). The gantry may be a ring or circular gantry, an arcuate gantry, a C-arm gantry, or a robotic arm gantry. One example of a therapeutic radiation source is a linear accelerator (linac). Other examples of therapeutic radiation sources may include, but are not limited to, high energy photons, radiation or particles produced by a radioactive isotope (e.g. iridium or cobalt-60), high energy electrons, a proton beam, a neutron beam and a heavy ion beam. One or more beam-shaping elements may be disposed in the beam path of the therapeutic radiation source to define a treatment plane. For example, beam-shaping elements may comprise a jaw and a dynamic multi-leaf collimator (MLC). The dynamic MLC may be a binary MLC or a 2-D MLC. A binary MLC may be one in which each leaf may be movable to, and retained at, an open configuration or at a closed configuration, while a 2-D MLC may be one in which each leaf may be movable to, and retained at, any set of locations between a fully open configuration and a fully closed configuration. The jaw may be located between the therapeutic radiation source and the MLC, or may be located below the MLC. Alternatively, a jaw may be a split jaw where a first portion of the jaw is located between the therapeutic radiation source and the MLC (i.e., an upper jaw), and a second portion of the jaw is located below the MLC (i.e., a lower jaw) and coupled to the first portion of the jaw such that both portions move together. The width of the jaw opening or aperture through which a radiation beam passes may be adjustable, and during a treatment session, the width of the jaw opening may be adjusted one or more times. Optionally, the jaw may be movable within the beam of the therapeutic radiation source such that a treatment plane defined by the jaw may shift in a direction that is parallel to the motion of the patient platform. Some variations of a radiation therapy system may comprise a radiation detector mounted on the gantry opposite the therapeutic radiation source. For example, some variations may comprise a MV radiation detector located opposite a linac.

The patient platform of a radiation therapy system may be configured to move within the patient treatment region along its longitudinal axis (i.e., along IEC-Y) such that patient target regions are sequentially moved through the therapeutic radiation beam plane. The patient platform may be configured to move continuously at a constant or variable speed during radiation delivery. Alternatively or additionally, the patient platform may be configured to move to discrete locations or beam stations and may be stationary at a beam station during radiation delivery. The rate and range of patient platform motion may be calculated before a treatment session and/or at the start of a treatment session. For example, the number of beam stations and location of beam stations (e.g., with respect to system isocenter) may be determined by the treatment planning system, and/or the rate at which the patient platform moves between beam stations may be selected by a clinician (e.g., based on desired treatment time and/or patient comfort). In some variations, the distance between beam stations (e.g., step distance, distance between two beam stations, including two adjacent beam stations) may be constant throughout the entire treatment session, or may be variable between different beam stations. For example, the step distance may be about 0.5 mm, about 1 mm, about 1.1 mm, about 1.5 mm, about 2 mm, about 2.1 mm, about 2.5 mm, about 3 mm, about 3.5 mm, about 4 mm or more, 10 mm or more, 1 cm or more, 2 cm or more, and may optionally, in some variations, correspond with the thickness of CT image slices used during treatment planning. Alternatively or additionally, step distance may be selected based on the resolution and/or thickness of the treatment planning image(s), and/or the resolution and/or thickness of any imaging systems used to acquire imaging data during a treatment session (e.g., PET imaging system, CT or X-ray imaging system, etc.), and/or the field size of a therapeutic radiation beam (e.g., less than or equal to the full-width half maximum of a dimension of the radiation beam). Beam station step distance may be adjusted so that the step distance is smaller where the fluence gradient of the planned/calculated fluence map to the patient target region is greater (e.g., at an edge of a patient target region) and may be larger where the fluence gradient to the patient target region is smaller (e.g., in a middle portion of a patient target region). The number of beam stations and the distance between the first beam station and the last beam station in a set of beam stations may be determined by a treatment planning system based on the size and location of the one or more patient target regions, and/or the current or desired width of the jaw opening. Alternatively or additionally, beam station step distance may be the same between each beam station, but if the fluence to be delivered at a particular beam station is zero, the patient platform may bypass/skip that beam station (e.g., not stop at that beam station, not activate the therapeutic radiation source when the patient platform is at that beam station) and move the platform to the next beam station where the fluence to be delivered has a non-zero value. This may result in the delivery of radiation at beam stations that are located at different distances from each (i.e., in multiples of the step distance value). For a continuously moving patient platform, the speed may be constant throughout radiation delivery, or may vary depending on the fluence gradient of the planned/calculated fluence map to the patient target region. For example, the speed of the patient platform may be lower where the fluence gradient of the planned/calculated fluence map to the patient target region is greater (e.g., at an edge of a patient target region, and/or a region with a relatively larger prescribed dose) and the speed may be higher where the fluence gradient to the patient target region is smaller (e.g., in a middle portion of a patient target region, and/or a region with a relatively smaller prescribed dose). A patient platform may comprise one or more position sensors, motion sensors, accelerometers, and/or encoders-decoders in communication with a controller of the radiation therapy system, so that the controller may monitor and/or confirm that the patient platform is located and/or oriented at a designated beam station prior to the emission of therapeutic radiation. For example, the X-, Y-, Z-, pitch, yaw, and roll values of a patient platform may be compared with the beam stations specified by the treatment plan, and if differences or deviations are detected, the controller may be configured to generate an audio and/or visual notification to the clinician.

A radiation therapy system may also comprise a system controller in communication with all of the components of a radiation therapy system, and may, for example, generate commands to the therapeutic radiation source, and/or gantry, and/or beam-shaping elements, and/or patient platform. The system controller may also comprise a processor and memory. A controller memory may store treatment plan data, segmentation data and/or instructions, as well as any data acquired by any sensors or detectors of the radiation therapy system (e.g., PET detectors, kV detector, MR sensors, MV detector, position sensors, motion sensors, accelerometers, and/or encoders-decoders). The controller processor may be configured to segment a treatment plan fluence map (or any fluence map that may be generated subsequent to the start of the treatment session) into machine instructions (e.g., MLC leaf configurations for each firing position at a particular beam station, linac pulse instructions), therapeutic radiation source emission properties/characteristics (e.g., pulse energy, pulse amplitude, pulse width, pulse frequency, duty cycle, etc.), and/or calculate delivered dose or fluence based on machine parameters (e.g., linac pulse frequency, duty cycle, energy, dose chamber, MLC leaf openings, etc.). A radiation therapy system may also comprise one or more displays and one or more speakers. The controller processor may be configured to generate visual and/or audio alerts/notifications that may be transmitted to the display and/or speakers.

Optionally, some radiation therapy systems may comprise one or more PET detectors, which may be mounted on the same rotatable gantry as the therapeutic radiation source, or on a separate/second gantry from the therapeutic radiation source that may or may not be rotatable about the patient treatment region. In some variations, the PET detectors and the therapeutic radiation source may be coplanar (i.e., imaging plane is coplanar with the treatment beam plane) or non-coplanar (i.e., imaging plane is not coplanar with the treatment beam plane). Lines-of-response (LORs) defined by a pair of 511 keV photons emitted by a positron annihilation event may be detected by the PET detectors and transmitted to a system controller. In some variations, a patient may be injected with a PET tracer prior to a treatment session, and LORs from the PET tracer may be detected by the PET detectors. The PET tracer may accumulate at patient regions with elevated metabolic rates, such as tumor regions. Alternatively or additionally to PET detectors, some radiation therapy systems may comprise a CT imaging system, X-ray imaging system, ultrasound imaging system, and/or MRI imaging system.

One variation of a radiation therapy system is depicted in FIG. 1. FIG. 1 depicts one variation of a radiation therapy system that may be used in beam station radiation delivery. The radiation therapy system (100) may comprise a gantry (102) rotatable about a patient treatment region (104), one or more PET detectors (106) mounted on the gantry, a therapeutic radiation source (108) mounted on the gantry, a beam-shaping module (110) disposed in the beam path of the therapeutic radiation source, and a patient platform (112) movable within the patient treatment region (104). The beam-shaping module (110) may comprise a movable jaw and a dynamic multi-leaf collimator (MLC). The beam-shaping module may be arranged to provide variable collimation width (e.g., the width of the treatment beam plane) in the longitudinal direction (e.g., IEC-Y) of 1 cm, 2 cm or 3 cm at the system iso-center (e.g., a center of a patient treatment region). In some variations, the treatment beam planes for adjacent beam stations may overlap (i.e., treatment beam plane width is similar to, or wider than, the distance between beam stations). The jaw may be located between the therapeutic radiation source and the MLC, or may be located below the MLC. Alternatively, the beam-shaping module may comprise a split jaw where a first portion of the jaw is located between the therapeutic radiation source and the MLC, and a second portion of the jaw is located below the MLC and coupled to the first portion of the jaw such that both portions move together.

The gantry (102) may be configured to rotate at a rate from about 15 RPM to about 70 RPM (e.g., about 50 RPM or more, about 60 RPM or more), the binary dynamic MLC may be configured to change leaf configurations within about 15 ms or less (e.g., about 10 ms or less, about 8 ms or less), and the patient platform (112) may be configured to move at a rate of about 0.5 mm/s or less. In some variations, the gantry may be a circular gantry. For example, a high-speed binary multi-leaf collimator may comprise leaf actuating mechanisms having a spring system that operates in concert with and is coupled to a pneumatic system to provide sufficient motive force to move a MLC leaf between open and closed configurations within the time constraints described above. The gantry (102) may move the linac (108) to discrete, pre-defined circumferential firing positions as it rotates. Some systems have about 50 firing positions or angles (e.g., from about 0° to about 360°, where each firing position is separated by a regular angular interval). Some systems may have about 100 firing positions. Alternatively or additionally, some systems may be configured to have a discrete set of firing positions at arbitrary angles around the patient platform (e.g., at 0°, 45°, 90°, 135°, 180°, etc.).

In some variations, the radiation therapy system may optionally comprise a first array of PET detectors (106a) and a second array of PET detectors (106b) disposed across from the first array, a linear accelerator (108) or linac, and a beam-shaping module (110) comprising jaws and a dynamic binary MLC. The system may further comprise a controller that is in communication with the gantry, PET detectors, linac, and MLC, where the controller has one or more memories that may store treatment plans, radiation-firing matrices, fluence maps, system instructions/commands, and a processor configured to execute the calculations and methods described herein. A patient located or disposed on the patient platform (112) within the patient treatment region (104) may have been injected with a PET tracer that emits positrons, and the PET tracer may accumulate at particular regions of the patient (e.g., such as tumor regions). The annihilation of a positron with a nearby electron may result in the emission of two photons traveling in opposite directions to define a LOR or positron annihilation emission path. PET detectors may detect one or more LORs. In some variations, the PET detectors may be time-of-flight PET detectors, which may help to identify the location of the positron annihilation event. A treatment plan fluence map may be updated using LOR data and/or PET imaging data and/or MV detector data (e.g., from a MV detector located opposite the linac (108) on the gantry) as the patient is moved through the patient treatment region (e.g., in pre-defined patient platform beam stations, or continuous patient platform movement through the patient treatment region and/or treatment plane). Optionally, radiation therapy system (100) may comprise a CT imaging system (e.g., a kV radiation source and a kV detector mounted across from the kV radiation source) mounted on the same gantry as the therapeutic radiation source or mounted on a separate gantry, and may be coplanar with the radiation source (i.e., imaging plane is coplanar with the treatment beam plane) or non-coplanar with the therapeutic radiation source (i.e., imaging plane is not coplanar with the treatment beam plane). Optionally, a radiation therapy system may comprise an optical imaging system (e.g., one or more optical sensors or cameras) mounted on the same gantry as the therapeutic radiation source, which may be configured to acquire patient images while the gantry rotates about the patient platform. Additional details and examples of PET-based radiation therapy systems are described in U.S. patent application Ser. No. 15/814,222, filed Nov. 15, 2017 which is hereby incorporated by reference in its entirety. Imaging data from the optional PET detectors, and/or kV detectors, and/or optical sensors may be configured to track patient position and/or motion (e.g., patient body shifts, breathing, fidgeting, etc.) so that radiation delivery may be adjusted to account for such motion. For example, radiation delivery may be synchronized (e.g., gated) with breathing motions so that radiation is delivered to the patient when the patient target region is located inside a treatment location and radiation is not delivered to the patient when the patient target region is located outside a treatment location.

While the examples and variations disclosed herein are described in the context of a radiation therapy system having a therapeutic radiation source (e.g., linac) mounted on a circular gantry that is configured to continuously rotate and/or step through firing positions about the patient platform (e.g., 360° rotation), it should be understood that treatment planning and radiation delivery methods described herein may be used with radiation therapy systems that do not have a continuously rotating circular gantry. For example, the treatment planning and radiation delivery methods described herein may be used with a radiation therapy system comprising a therapeutic radiation source mounted on a robotic arm or an arcuate or C-shaped gantry. The travel path of the patient platform may be along a longitudinal axis (e.g., IEC-Y) and the arm or C-shaped gantry may be located away from the travel path of the patient platform (e.g., not located along the longitudinal axis). For example, a radiation therapy system may comprise a patient platform configured to move and stop at predetermined, discrete locations along a longitudinal axis (e.g., beam stations), a therapeutic radiation source, and a movable arm or gantry to which the therapeutic radiation source may be mounted, where the arm or gantry (e.g., C-shaped gantry) is configured to move the radiation source about the patient platform. The arm or gantry may be located on either side of the longitudinal axis so that platform motion is not impeded, but the arm or gantry may move the therapeutic radiation source above the platform to various locations (some of which may be parallel to the longitudinal axis) so that radiation may be applied to a patient on the platform from multiple firing positions. Optionally, such radiation therapy systems may comprise an imaging system (e.g., PET, CT, X-ray, MRI, ultrasound, etc.) that may be mounted on the same or different arm or gantry from the therapeutic radiation source, and may also be positioned at a location that is not in the travel path of the patient platform. While the radiation therapy system in FIG. 1 is an open-bore system, the methods described herein may also be used with a closed-bore system.

Beam Station Treatment Planning Methods

A treatment planning system may be configured to generate a fluence map that is suitable for beam station delivery. A treatment planning method may comprise identifying one or more patient target regions from a set of images (e.g., CT images) and user-defined contours, prescribing a desired dose distribution to the one or more target regions, and calculating a fluence map comprising a set of radiation beamlets that when delivered, will deliver radiation according to the desired dose distribution. Some treatment planning methods may comprise calculating and optimizing dose on a beam station basis, where the treatment plan may comprise one or more fluence maps (and/or optionally, dose maps) for each beam station. For example, in some variations, the beam station step distance may match the slice thickness of the planning CT images, and a treatment planning method may comprise calculating a 2D fluence map for each beam station, where the fluence map representing the fluence to-be-delivered at a particular beam station in order to attain an overall dose distribution as prescribed by a clinician. Each 2D fluence map slice may be a l×f matrix, which l is the number of leaves in the dynamic MLC (e.g., a binary MLC), and f is the number of firing positions. Each entry of the l×f matrix may represent the configuration and/or position of a MLC leaf l when the therapeutic radiation source is located at a firing position f. For example, a fluence map generated by a treatment planning system for a radiation therapy system having a 64-leaf binary MLC and 51 firing positions around a continuously rotatable gantry may be a (64×51) matrix, representing each of the 64 leaves at each of the 51 firing positions. Some treatment plans for beam station delivery may generate one or multiple fluence maps for each beam station, depending on the prescribed dose at that beam station and the amount of radiation deliverable by the radiation therapy system over a single revolution around the patient platform. In some variations, fluence map calculations for a beam station may assume that all firing positions at a given beam station may be used to deliver radiation beamlets. For example, a treatment planning method may calculate fluence maps based on 50 firing positions, though delivery may be implemented by delivering the fluence for one firing position over 2 adjacent sub-firing positions. In this example, a treatment planning method may further calculate sub-fluence maps for each of the sub-firing positions, thereby generating 100 sub-fluence maps for 100 sub-firing positions. Some variations of treatment planning methods may comprise defining a set of beam stations (e.g., the locations and/or orientations where a patient platform may be stopped during the delivery of therapeutic radiation, number of beam stations, and/or step distance between beam stations), dwell time per beam station, fluence and/or dose maps for each beam station, jaw configuration (e.g., jaw width) for each beam station, and/or therapeutic radiation source (e.g., linac) pulse parameters, and/or the number of times each patient target region crosses or passes through the treatment plane (e.g., therapeutic radiation beam plane).

As described herein, the number and location of beam stations and beam station step distance(s) may be determined during treatment planning. In some variations, a clinician may specify a desired beam station step distance (e.g., which may match the slice thickness of CT planning images, and/or may be an absolute step distance or pitch value such as about 2.1 mm, etc.). For example, for a beam station step distance or pitch of about 2.1 mm, the treatment planning system may perform 3D dose optimization for the patient target regions identified in the planning CT images, with the planning CT grid recalculated at fixed spacing of 2.1 mm for all patient target regions. The number and location of beam stations may be determined by the size and/or location of the one or more patient target regions and the beam station step distance. For example, larger patient target regions, or patient target regions that are located far apart from each other, may be allocated a greater number of beam stations than smaller target regions, or target regions that are located close to each other. Alternatively or additionally, the distance between beam stations may be determined by the jaw opening settings. For example, larger beam station step distances may be selected for jaw opening widths of about 1 cm, about 2 cm, or about 3 cm or more. In some variations, the beam station step distance may be uniform across a set of beam stations while in other variations, the beam station step distance may not be uniform across a set of beam station stations. In some variations, the treatment beam planes for adjacent beam stations may overlap (i.e., treatment beam plane width is similar to, or wider than, the distance between beam stations). Alternatively or additionally, beam station step distance may be selected based on the resolution and/or thickness of the treatment planning image(s), and/or the resolution and/or thickness of any imaging systems used to acquire imaging data during a treatment session (e.g., PET imaging system, CT or X-ray imaging system, etc.), and/or the field size of a therapeutic radiation beam (e.g., less than or equal to the full-width half maximum of a dimension of the radiation beam). In some variations, the number of beam stations and/or step distance may be determined on a clinic-wide basis and/or may be a hardware constraint or mode of the radiation therapy system that is set during manufacturing and/or upon system installation. In some variations, the distance between beam stations may vary depending on the fluence gradient for a patient target region. For example, beam stations that overlay with areas of high fluence gradients (e.g., an edge or boundary of a patient target region), the beam station step distance may be smaller than for beam stations that overlay with areas of low (or no) fluence gradients (e.g., a central portion of a patient target region).

As described previously, a beam station may be any platform location and/or orientation determined during treatment planning where the platform is stopped or static during the emission of therapeutic radiation. While the patient platform is in motion (e.g., moving from one beam station to another), the therapeutic radiation source does not emit radiation to the patient. In some variations, beam station locations designated by a treatment planning system may all be located on a plane defined by IEC-X and IEC-Y axes. That is, the trajectory of a patient platform in the course of a treatment session may be on a single plane (e.g., a horizontal plane with little or no vertical motion). For example, the set of beam stations selected by a treatment planning system may be located along a line along the IEC-Y axis (e.g., a linear trajectory), and/or may be located on a non-linear (e.g., along one or more curves and/or multiple line segments which may or may not be collinear) trajectory on a plane. A treatment planning system may designate beam stations that are not all located on a single plane as defined by IEC-X and IEC-Y. That is, the trajectory of a patient platform in the course of a treatment session may not be confined to a single plane, but may be located in two or more planes in 3D space. For example, a beam station may be specified by coordinates in IEC-X, -Y, and -Z, and/or may be specified by the orientation of the patient platform (e.g., roll, yaw, and pitch of the patient platform). Different beam stations may have the same X-, Y- and/or Z-coordinates, but may have different patient platform orientations (e.g., different roll values, yaw values, and/or pitch values). Alternatively or additionally, different beam stations may have the same patient platform orientations (e.g., same roll values, yaw values, and/or pitch values), but have different X-, Y- and/or Z-coordinates. Beam stations where the patient platform is tilted (e.g., having non-zero roll values, yaw values, and/or pitch values) may allow for non-coplanar delivery of radiation to irradiate target regions that may be adjacent to (e.g., located behind) an OAR. While the examples and variations of methods described herein define beam stations that form a linear trajectory along IEC-Y during a treatment session, it should be understood that similar methods may be used with beam stations that form any non-linear and/or non-coplanar trajectory in two or more dimensions, and that beam stations may differ from each other by patient platform orientation values.

In addition or alternative to determining the number and/or location of beam stations by the size and/or location of the one or more patient target regions, the number and/or location of beam stations may be determined by whether any patient-positioning devices will be used during the delivery of therapeutic radiation. For example, if a head-positioning device (e.g., a head-tilting device or pillow) is to be used during a treatment session to orient the patient's head in a particular manner (e.g., with a particular tilt, etc.), treatment planning methods may calculate the location of one or more beam stations to account for the orientation of the head-positioning device. Alternatively or additionally, if it is determined that a prescribed dose distribution may be more accurately delivered if the position of at least a portion of the patient is adjusted or secured by a patient positioning device to have a particular orientation and/or location, treatment planning methods may calculate the location of one or more beam stations based on the assumption that at the time of treatment, a patient positioning device will be provided and configured to provide that particular orientation and/or location.

In some variations, treatment planning methods may comprise determining the number of times that a patient target region passes through the therapeutic radiation beam plane or treatment plane. For example, the patient platform of the radiation therapy system may move a patient through the treatment plane a first time in a first direction (e.g., moving forward along the IEC-Y axis) and then a second time in a second direction (e.g., moving backward along the IEC-Y axis) opposite to the first direction. Each patient platform "pass" may comprise moving patient platform in one direction such that all of the patient target regions have crossed the treatment plane once. Treatment planning methods may comprise determining the number of passes and determining a set of patient platform beam stations and corresponding fluence map(s) for each pass in order to deliver the prescribed dose to each patient target region. In some variations, a first pass may comprise a first set of beam stations (e.g., patient platform locations and/or orientations) and a second pass may comprise a second set of beam stations where one or more of the beam stations in the second set may be the same as, or different from, the beam stations in the first set. For example, a first set of beam stations for a first pass may comprise patient platform locations at IEC-Y coordinates 1 mm, 3 mm, 5 mm, 7 mm, 9 mm, . . . , 99 mm, while a second set of beam stations for a second pass may comprise patient platform locations at IEC-Y coordinates 2 mm, 4 mm, 6 mm, 8 mm, . . . , 100 mm (traversed in either the same direction as the first pass or in an opposite direction). Staggering or alternating the beam stations between different passes may facilitate more granular delivery of therapeutic radiation and/or super-sampling of imaging data by an imaging system (e.g., PET detectors, X-ray detectors, etc.) that is mounted on the same gantry as the therapeutic radiation source. Alternatively, the IEC-Y coordinates for both the first and second passes may be the same. Optionally, the IEC-Y coordinates may be the same for the beam stations in the first and second sets, while the platform orientation (e.g., pitch, yaw, roll values) may vary between the first and second sets of beam stations. Some variations of treatment planning methods may comprise calculating the number of passes, the set of beam stations for each patient platform pass, fluence map(s) for each beam station for each pass, and/or the dwell time for each beam station (and/or the number of therapeutic radiation source gantry rotations or translations per beam station). Additional details regarding multi-pass delivery (e.g., shuttle mode delivery) are provided in U.S. patent application Ser. No. 16/138,631, filed Sep. 21, 2018, which is hereby incorporated by reference in its entirety.

The duration time that a patient platform spends at a beam station may be referred to as "dwell time". For radiation therapy systems comprising a therapeutic radiation source mounted on a continuously rotating (e.g., 360° rotation) circular gantry, dwell time may also be represented by the number of gantry rotations or revolutions while the patient platform is at a beam station (e.g., number of revolutions multiplied by the period of a revolution). While a patient platform is at a beam station, the therapeutic radiation source may emit radiation for the entire dwell time, or for a portion of the dwell time. For example, if the dwell time for a beam station is 10 seconds, the therapeutic radiation source may emit radiation to the patient for any duration of time from about 0.5 second up to about 10 seconds (and may not emit radiation for the remainder of the time). Alternatively, if dwell time is represented by the number of gantry rotations R, the therapeutic radiation source may emit radiation to the patient during r rotations, where r≤R, and may not emit radiation during the other (R−r) rotations. For example, if the dwell time is 10 rotations, the therapeutic radiation source may deliver radiation during just 1 rotation (i.e., 9 rotations with no radiation delivery), 2 rotations (i.e., 8 rotations with no radiation delivery), etc. up to 10 rotations. Although the dwell time for each beam station in a set of beam stations may be the same, the amount of radiation delivered at each beam station could vary widely and allow for high dose modulation across beam stations, depending on the amount of time and/or number of gantry rotations during which the therapeutic radiation source emits radiation. The dwell time (i.e., represented in temporal units such as seconds or minutes, or number of gantry revolutions) at each beam station may be determined during treatment planning by one or more factors (alone or in combination), including but not limited to, the gantry rotation speed, and/or number of gantry revolutions to deliver a fluence map, and/or fluence gradient, and/or jaw opening width settings. Optionally, in addition to these factors, the dwell time at each beam station may also be determined by any clinical factors or treatment parameters selected by a clinician, such as overall treatment time, correspondence to planning image slice thickness or position (e.g., CT or PET image slice thickness), and the like. The dwell time (or number of gantry revolutions) may vary per beam station, or may be constant across all beam stations. For example, the number of revolutions per beam station may be from about 2 to about 300 (e.g., from about 2 to about 5 revolutions, from about 4 to about 7 revolutions, from about 6 to about 10 revolutions, from about 10 to about 15 revolutions, from about 18 to about 24 revolutions, from about 30 to about 45 revolutions, from about 40 to about 50 revolutions, from about 50 to about 100 revolutions, from about 100 to about 120 revolutions, from about 5 to about 150 revolutions, from about 2 to about 200 revolutions, from about 100 to about 200 revolutions, from about 150 to about 250 revolutions, from about 200 to about 300 revolutions, etc.). The dwell time at a beam station may be from about 5 seconds to about 8 minutes (e.g., from about 5 to about 7 seconds, from about 5.5 to about 6.5 seconds, from about 7 to about 10 seconds, from about 6 to about 15 seconds, from about 5 to about 20 seconds, about 20 seconds or more, from about 20 to about 30 seconds, from about 5 to about 60 seconds, from about 20 to about 120 seconds, from about 60 to about 300 seconds, from about 5 to about 400 seconds, about 350 seconds or more, from about 5 to about 300 seconds, etc.). Some radiation therapy systems may have a fast-spinning gantry that is configured to rotate a linac about a patient platform at about 60 RPM, where the dwell time for each beam station may be less than about 20 seconds and/or sufficient time for at least two gantry revolutions (and up to about 480 seconds), and from about 20 to about 25 revolutions (and up to about 300 revolutions). In some variations, for example, intensity-modulated radiation therapy (IMRT) and delivery, the number of revolutions per beam station may not be constant, and may be determined by the treatment planning system before the treatment session. In some variations, the dwell time for some beam stations may be substantially longer than for other beam stations. For example, the first and last beam stations may have longer dwell times (e.g., more revolutions) than intermediate beam stations. Dwell time at the edges/boundaries of target regions may be greater than at center areas of target regions due to the complex contours of the edge/boundary areas. Complex or irregular contours may require multiple MLC configurations, delivered over multiple revolutions, in order to deliver radiation with the prescribed precision. In some variations, for example, radiation delivery based upon PET imaging data (e.g., biologically-guided radiation therapy or BGRT), the number of revolutions (or dwell time) per beam station may not be calculated during treatment planning, but may instead be calculated by the radiation therapy system controller during the treatment session (e.g., just prior to radiation delivery at a beam station). Alternatively or additionally, all beam stations may have the same dwell time (or number of revolutions).

In some variations, the dwell time may be calculated during treatment planning and updated during the treatment session. One variation of a method for calculating dwell time may comprise determining the amount of fluence (e.g., in MU) to be delivered at a beam station in order to comply with the prescribed dose, determining the fluence emission rate of the therapeutic radiation source (e.g., in MU per unit of time, in MU per gantry rotation), and dividing the amount of fluence to be delivered by the fluence emission rate of the therapeutic radiation source to obtain the amount of time or number of revolutions a patient platform is to remain at the beam station in order to deliver the prescribed dose. The fluence emission rate may depend, for example, on the dose rate, pulse frequency, pulse width, etc. Another variation of a method for calculating dwell time may comprise segmenting the fluence map(s) for a beam station into a set of radiation therapy system machine instructions, including MLC configurations, and determining the number of gantry revolutions and/or MLC configurations in order to deliver the fluence map(s). A complex target region geometry (e.g., at the edge of a target region) may need more binary MLC configurations to approximate that geometry than a target region with less complex geometry (e.g., in a central portion of a target region). In some variations, a treatment planning method may set the dwell time for all beam stations to the longest dwell time of the beam station set. The estimated treatment session time may be calculated by multiplying the longest dwell time by the number of beam stations, and optionally, the number of passes. Alternatively, the dwell time may be beam station specific, and the estimated treatment session time may be calculated by summing the dwell time for all beam stations, and optionally, multiplying the sum by the number of platform passes. In some variations, the number of gantry rotations (e.g., 360° revolutions of a circular gantry, 180° sweeps of a gantry) per beam station may be at least two or more, e.g., about 50, about 100, about 200, about 300 gantry rotations, etc. Alternatively or additionally, the dwell time per beam station may be about 20 seconds, about 50 seconds, about 100 seconds, about 120 seconds, about 150 seconds, etc. The actual dwell time during a treatment session may vary from the estimate generated during treatment planning depending on whether any system components malfunctioned during the treatment session, as well as the location and/or geometry of the target region(s) at the time of treatment.

Figure 2A:
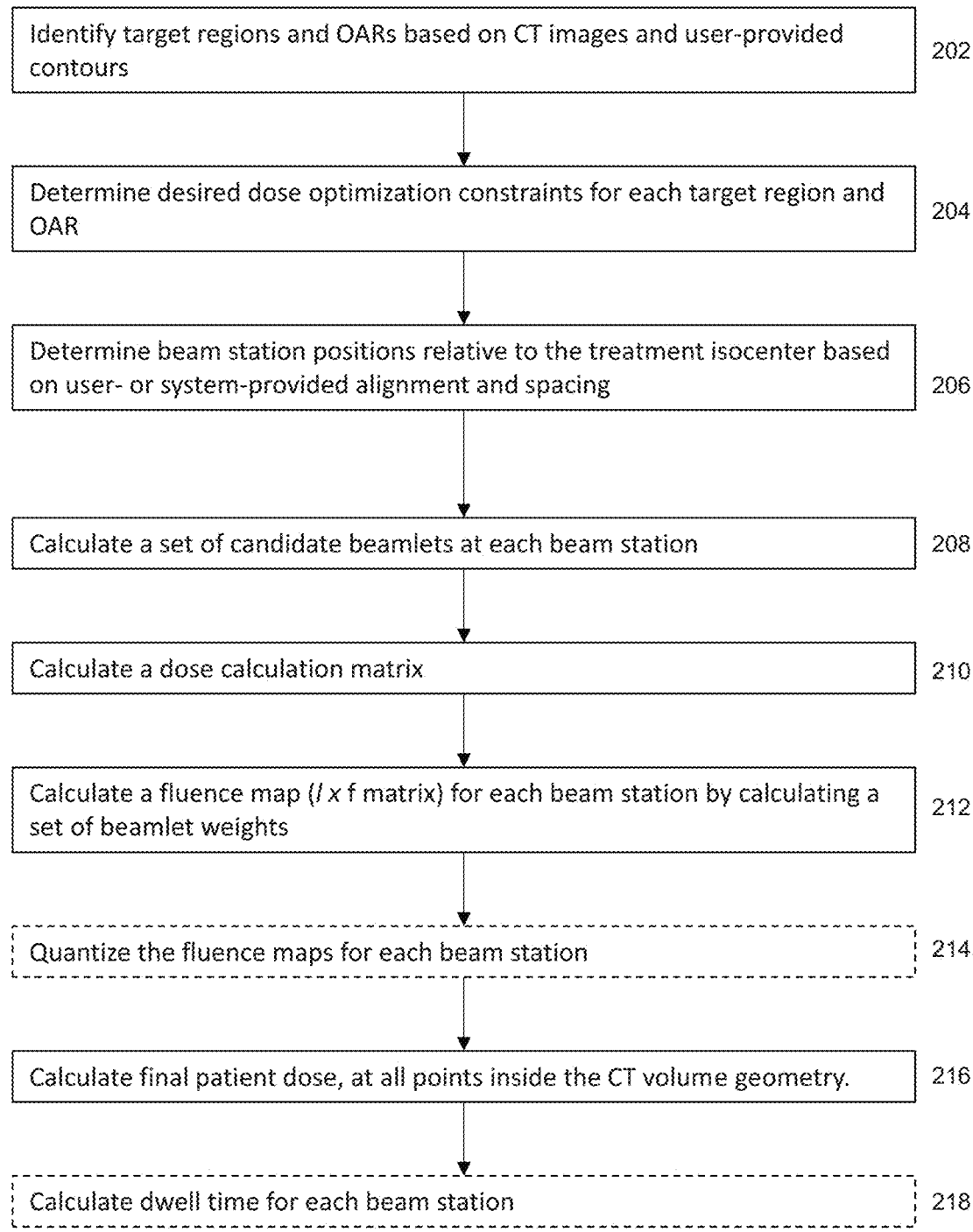
FIG. 2A depicts a flowchart representation of one variation of a method for treatment planning for beam station delivery.

One variation of a treatment planning method for beam station delivery by a radiation therapy system with a binary MLC is depicted in FIG. 2A. Method (200) may comprise identifying (202) patient target regions and organs-at-risk (OARs) based on planning images (e.g., CT images) and clinician-provided contours and identifying the system isocenter relative to the planning images (i.e., treatment isocenter), and determining (204) desired dose optimization constraints for each target region and OAR based on clinician-provided dose prescription information. Examples of dose optimization constraints may include maximum dose thresholds to certain structures (e.g., target regions or OARs), mean dose over target regions or OARs (e.g., maximum mean dose of 25 Gy to the kidneys or minimum mean dose of 50 Gy to a target region), specified amounts of tissue volumes at specific dose values, and equivalent uniform dose (EUD) values (e.g., EUD to compensate for heterogeneous delivery of dose, minimum EUD of 50 Gr at 0.35 α). Examples of dose prescription information may include radiation dose amounts per target region or OAR volume (e.g., >95% coverage of target volume at 50 Gy, no more than 15 cc of lunch tissue at 20 Gy, at least 50% of target volume at 50 Gy, etc.). Other examples of dose metrics may include, but are not limited to, critical organ scoring index (COSI), conformation number (CN), conformity index (CI), target coverage index (TCI), prescription isodose to target volume (PITV) ratio, homogeneity index (HI), modified dose homogeneity index (MHI), and/or quality factor (QF), and the like. Some variations may include constraints such as biological metrics, for example, the generalized equivalent uniform dose (gEUD), normal tissue complication probability (NTCP), and/or tumor control probability (TCP). Method (200) may comprise determining (206) beam station positions relative to the treatment isocenter based on clinician- or system-provided alignment and spacing and mapping beam station positions to corresponding patient platform positions. As described above, the number and location of a set of beam stations, along with the platform X-, Y-, Z-coordinates and orientations for each beam station may be determined based on the number, location, size and shape of the patient target region(s). For example, the first beam station of a set of beam stations may be located at or around the inferior-most boundary of the inferior-most patient target region and the last beam station of the set of beam stations may be located at or around the superior-most boundary of the superior-most patient target region. The treatment isocenter may be aligned with a beam station or may be offset from the beam stations, and the distance between beam stations may be selected or calculated as described previously.

After determining beam station positions, method (200) may comprise calculating (208) a set of candidate radiation beamlets for each beam station. A radiation beamlet may be a portion of a full radiation beam from the therapeutic radiation source, where the beamlet is defined by a multi-leaf collimator leaf opening at a particular firing position with respect to the patient area. That is, a beamlet may be designated by (l, f, b), representing the radiation applied to the patient area when the therapeutic radiation source is located at firing position f, the patient platform is at beam station b, and the open/close state of binary MLC leaf l. In some variations, a beamlet may be further defined by the width of the jaw opening, which may vary per beam station or may be the same for all beam stations (e.g., as described in the examples provided herein). A candidate beamlet for beam station b is a beamlet that intersects a patient target region when the platform is located at beam station b.

Method (200) may then comprise calculating (210) a dose calculation matrix for each beam station that represents the dose contribution of each candidate beamlet to all the patient target region(s) and OAR(s), assuming a beamlet intensity or beamlet weight of 1. In some variations, the dose calculation matrix may be calculated based on the dose contribution of each candidate beamlet to a set of sampling points or voxel selected for each target region and OAR. Calculating the dose matrix on a set of sampling voxels instead of all of the voxels of a target region or OAR may help reduce the computational resources (e.g., processor speed and memory usage) for this and other treatment planning calculations and optimization iterations, which may in turn reduce the computation time for completing such calculations.

After calculating a dose calculation matrix for each beam station, method (200) may comprise calculating a (212) fluence map for each beam station by calculating a set of candidate beamlet intensities or weights using a dose optimization technique. Beamlet weight or intensity is a measure of the dose from a therapeutic radiation source in arbitrary discrete units, and may be, for example, represented by the number of linac pulses, pulse amplitude, pulse width, leaf open time, and the like. Non-candidate beamlets (i.e., beamlets that do not intersect a target region) have beamlet weights of zero. Dose optimization techniques calculate a set of beamlet weights that, when delivered, matches or closely approximates the prescribed dose to the target regions while meeting specific dose constraints and/or treatment parameters. Dose constraints and treatment parameters may be specified by a clinician, and may include, for example, treatment plan quality metrics, maximum and minimum dose levels, dose distribution characteristics, treatment time, dose modulation across beam stations, and the like (including, but not limited to, the dose optimization and dose prescription parameters and constraints described above). In some variations, dose optimization methods may comprise aggregating one or more of the constraints and parameters into one or more penalty functions, and the optimization methods may be directed to reducing the value of the penalty function(s) while attaining the prescribed dose objectives. For example, dose optimization methods may calculate a set of candidate beamlet weights that minimize the value(s) of one or more penalty function while maximizing one or more treatment plan quality metrics. A fluence map pairs a particular beamlet ($l_0$, $f_0$, $b_0$) with a beamlet weight that designates the amount of radiation (i.e., fluence) to be delivered when the therapeutic radiation source is at firing position $f_0$, and the patient platform is at beam station $b_0$. For a given beam station, a beamlet can be specified by the MLC leaf index (e.g., leaf 1-64) and firing position (1-50), i.e., ($l_0$, $f_0$) in a l×f matrix, where l is the number of MLC leaves and f is the number of firing positions.

Method (200) may then optionally comprise quantizing (214) the fluence maps for each beam station so that each beamlet weight is an integer multiple of dose quanta deliverable by the therapeutic radiation source (e.g., linac). The dose quanta can be calculated based on, for example, a set of linac pulses and the pulse widths for each of the linac pulses in the set. For example, if for each firing position the linac can fire two linac pulses, and each of those pulses can be one of two pulse widths, then there are four different, discrete quanta for each firing position. Method (200) may comprise calculating (216) the cumulative patient dose over all fluence maps and all beam stations. In some variations, the cumulative dose distribution may be displayed to a clinician for approval. Optionally, method (200) may comprise segmenting the fluence map(s) for each beam station into machine instructions for execution by the radiation therapy system. The machine instructions may be provided to the radiation therapy system and/or may be used to estimate/calculate dwell time, as described below. In some variations, the fluence map(s) for each beam station are provided to the radiation therapy system, and the controller for the radiation therapy system segments the fluence map(s) into machine instructions, e.g., during the treatment session.

Optionally, method (200) may comprise calculating the dwell time for each beam station so that a clinician can estimate the length of a treatment session. The dwell time (DW) at a beam station ($b_0$) may be calculated based on the rotation speed of the gantry (e.g., revolution time or RevT), highest beamlet weight of the set of beamlet weights for that beam station (Max-Weight(b)), and the maximum amount of dose that deliverable at a single firing position in a single pass or revolution (Max-Dose-fp), for example:

$$DW(b_0) = \text{RevT} * \text{Max-Weight}(b_0) / \text{Max-Dose-}fp$$

Where both Max-Weight($b_0$) and Max-Dose-fp have units of dose. The aggregate of the dwell times for all beam stations may provide an approximation of overall treatment time:

$$\text{Radiation delivery time} = \sum_{i=0}^{B-1} DW(b_i)$$

Where B is the total number of beam stations.

Figure 2B:
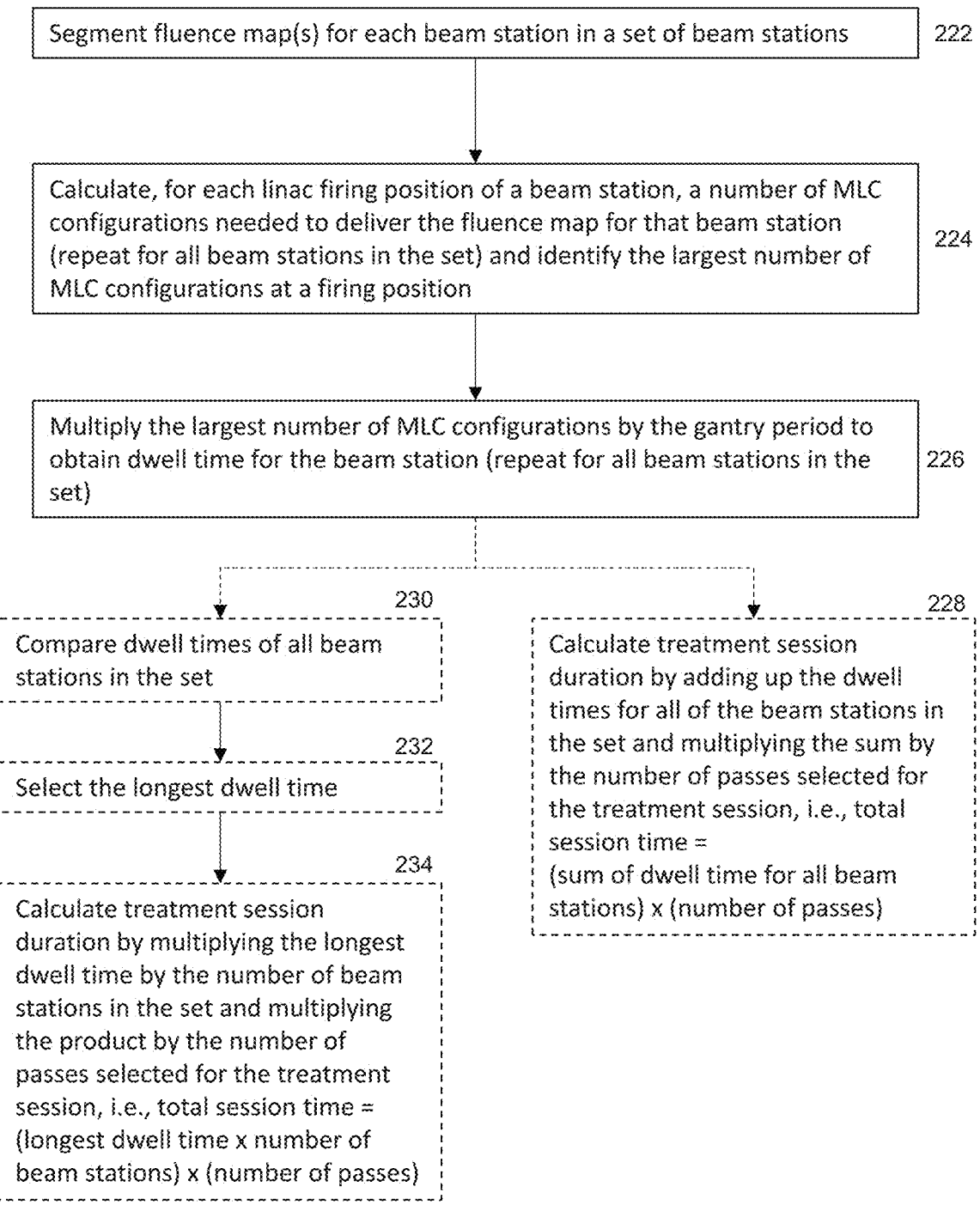
FIG. 2B depicts a flowchart representation of one variation of a treatment planning method for calculating beam station dwell time and treatment session duration.

Alternatively or additionally, beam station dwell time may be calculated based on segmented fluence map(s) for each beam station. Although the radiation therapy system instructions of the segmented fluence map may not necessarily be executed by the radiation therapy system during a treatment session (which may, in some variations, segment fluence maps in real-time), such "simulated segmentation" machine instructions may help to provide a more precise or realistic estimate of beam station dwell time and by extension, the treatment session duration. One variation of a method for calculating beam station dwell time and treatment session duration is represented by the flowchart in FIG. 2B. A method (220) for calculating beam station dwell time and/or treatment session duration may comprise segmenting (222) the fluence map(s) for each beam station in a set of beam stations into radiation therapy system machine instructions, calculating (224), for each linac firing position of a beam station, the number of MLC configurations needed to deliver radiation according to the fluence map for that beam station and identifying the largest number of MLC configurations at a firing position, and multiplying (226) the largest number of MLC configurations by the gantry rotation period (e.g., time per gantry revolution) to obtain the length of time the patient platform remains at that beam station. In some variations, method (220) may comprise calculating for each beam station the number of gantry revolutions needed to deliver the monitoring units (MUs) specified by the fluence map for that beam station, and the dwell time for that beam station may be calculated by determining the greater of the number of gantry revolutions for MU delivery and the number of MLC configurations, and multiplying the greater number by the gantry period. Optionally, the method (220) may comprise calculating (228) the treatment session duration by adding up all of the dwell times for all of the beam stations in the set of beam stations. If there are multiple patient platform passes, then the method may comprise multiplying the sum of the dwell times by the number of passes. Alternatively, to calculate the treatment session duration, the method (220) may comprise comparing (230) all of the dwell times of all of the beam stations in the set of beam stations, selecting (232) the longest dwell time of all of the beam station dwell times, and calculating (234) the session duration by multiplying the longest dwell time by the number of beam stations in the set. If there are multiple patient platform passes, the method may further comprise multiplying the product of the longest dwell time by the number of beam stations, with the number passes. Additional gantry rotations at a beam station may be included in order to deliver a greater quantity of fluence and/or to deliver fluence to a patient target region with a complex geometry (e.g., at an edge, where edge contour is best approximated by the sum of multiple binary MLC configurations). Although setting the dwell time for all beam stations to be the longest dwell time may appear to unnecessarily prolong the overall treatment time since the fluence at some beam stations do not need the entire dwell time for delivery, any "extra" dwell time at a beam station may be used to deliver missed and/or residual fluence that may result from machine malfunctions, and/or may be used to accommodate fluence changes due to any longitudinal patient target shifts, increases in fluence levels are indicated by the condition of the patient on the day of treatment, and/or compensating for fluence that may not have been deliverable at other beam stations.

As described previously, the width of a jaw opening may also be varied or adjusted on a beam station basis. Enlarging the jaw opening width may help to expedite dose delivery by increasing a dimension of each beamlet for example, by increasing the minimum dose per beamlet, which may be proportional to the dimension of each beamlet. This may be particularly efficient where the fluence gradient for a target region is relatively low (i.e., relatively constant fluence) so that a greater portion of the target region is irradiated per radiation pulse. The jaw opening width may be modulated during treatment planning (e.g., during dose optimization) or may be selected by a clinician. Alternatively or additionally, the jaw opening width may be a fixed value for all beam stations. In some variations, the treatment beam planes for adjacent beam stations may overlap (i.e., treatment beam plane width is similar to, or wider than, the distance between beam stations). For example, the distance between beam stations may be about 2.1 mm while the width of the treatment plane may be from about 10 mm to about 20 mm. In some variations, a treatment plan may specify that the jaw opening width is wider at an earlier portion of the treatment session than at a later portion of the treatment session. For example, the jaw opening width may be set to a first width $W_1$ for a first patient platform pass and then set to a second width $W_2$ for a second patient platform pass, where $W_2$ is less than (i.e., narrower than) $W_1$. This may help deliver fluence to larger regions (e.g., central portions of patient target regions) earlier in the session and facilitate the delivery of fluence to smaller regions (e.g., edge portions of patient target regions) later in the session. This may help expedite the delivery of radiation to large patient target regions. Some treatment planning methods may comprise calculating the dose distribution for each jaw opening width to determine the optimal fluence map for each beam station at each contemplated jaw opening width (and optionally for each pass).

Figure 2C:
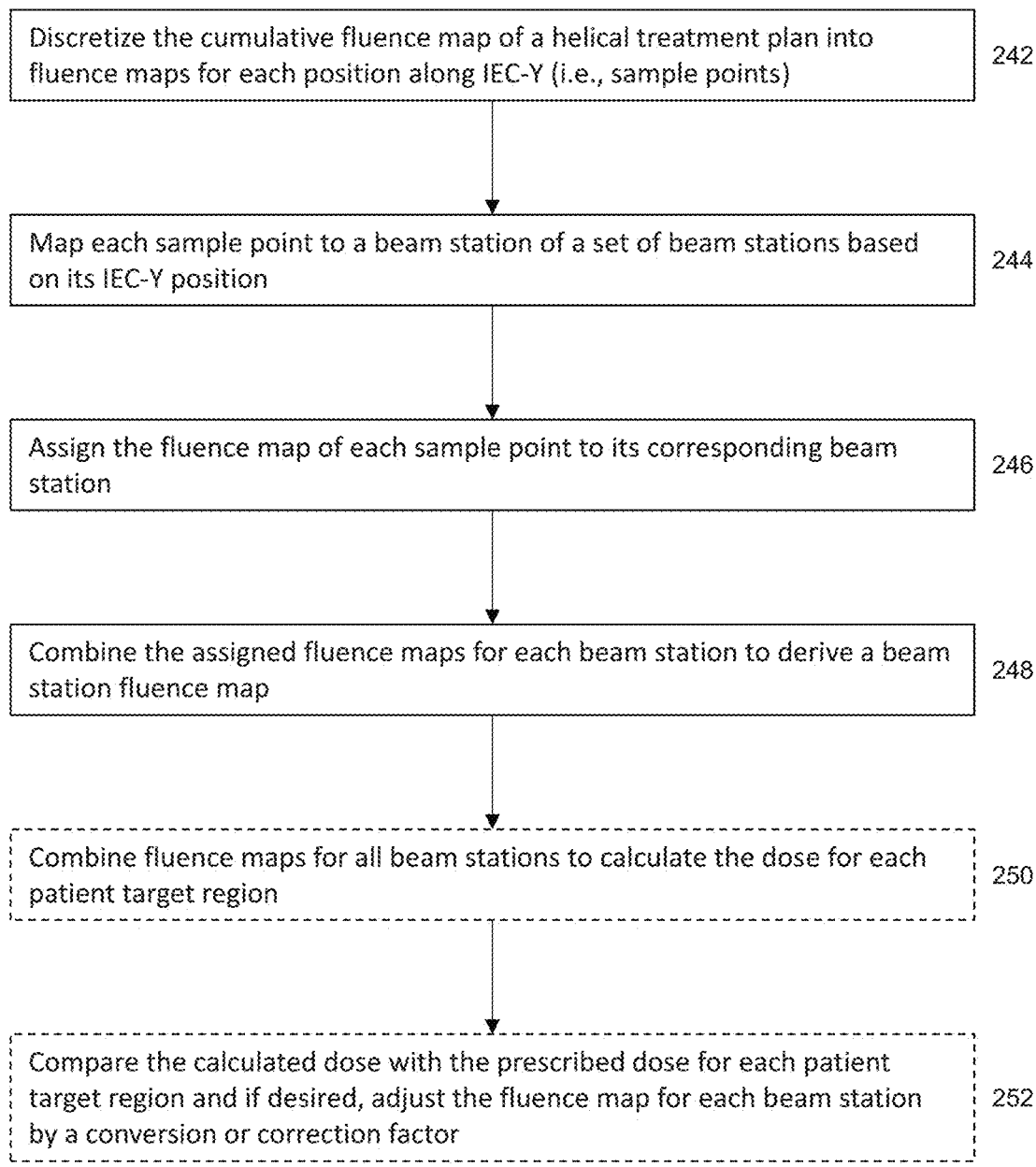
FIG. 2C depicts a flowchart representation of one variation of a method for converting a treatment plan for helical radiation delivery to a treatment plan for beam station delivery.

A treatment plan that has been developed for helical delivery (i.e., where the patient platform is in motion during therapeutic irradiation) may be converted into a treatment plan for beam station delivery (i.e., where the patient platform is stopped at specified beam stations during therapeutic irradiation). The "helical" descriptor represents the trajectory of the therapeutic radiation source relative to the continuously-moving patient platform (e.g., along IEC-Y axis). A helical treatment plan may specify the fluence to be emitted at each therapeutic radiation source firing position on the gantry (e.g., firing angle on a circular gantry) when the patient platform is at a particular location along IEC-Y. One variation of a method for converting a helical delivery treatment plan to a beam station delivery treatment plan is depicted in FIG. 2C. Method (240) may comprise discretizing (242) the cumulative fluence of a helical treatment plan into fluence maps for each position along IEC-Y (which may be referred to as sample points), mapping (244) each sample point to a beam station of a set of beam stations based on its IEC-Y position, assigning (246) the fluence map of each sample point to its corresponding mapped beam station, and combining (248), for each beam station, the fluence maps that have been assigned to it to derive a beam station fluence map. In some variations, the beam station fluence map for all of the beam stations may be quantized and/or segmented into radiation therapy system machine instructions, which may be transmitted to a radiation therapy system for execution during a radiation therapy session. Alternatively, the beam station fluence map for all of the beam stations may be combined and transmitted to the radiation therapy system for quantization and/or segmentation into machine instructions during a treatment session. As described elsewhere, in some variations, the fluence map for a beam station may be updated and/or adjusted (e.g., normalized) using imaging data acquired during the treatment session. Optionally, method (240) may further comprise combining (248) the fluence maps for all beam stations to calculate the dose to be delivered to each patient target region, comparing (252) the calculated dose with the prescribed dose for each patient target region, and if desired, the fluence map for each beam station may be adjusted by a conversion or correction factor. For example, if the cumulative fluence maps of all beam stations do not converge to the prescribed dose distribution for the patient, the fluence maps of one or more beam stations may be adjusted (e.g., scaled, reduced, and/or increased) by an adjustment or correction factor calculated based on the difference(s) between the calculated dose and the prescribed dose. The spacing (e.g., pitch) of the sample points along IEC-Y (i.e., the longitudinal axis of the patient platform and the axis along which the platform is moved) may be pre-selected, and the beam station parameters may be selected based on the characteristics of the helical trajectory. For example, the distance between beam stations may match or correspond with the pitch between the sample points along IEC-Y, and/or the time between sample points (or groupings of sample points) may correspond to a beam station dwell time, and/or the orientation and/or location of the beam station may correspond with the patient orientation and/or location. Conceptually, discretizing (242) the cumulative fluence map of a helical treatment plan sections the cumulative fluence map into helical segments or "slices" along IEC-Y. In some variations, a "slice" of fluence may represent the fluence delivered in an full revolution of the therapeutic radiation source across a "width" that corresponds to the pitch between sample points. Each fluence "slice" may be binned or mapped to a beam station based on its IEC-Y location. After the helical treatment plan has been converted to a beam station treatment plan, it may be quantized, segmented, and delivered as described elsewhere herein.

Beam Station Radiation Delivery Methods

Fluence maps for each beam station generated by a treatment planning system, along with other radiation delivery and dose calculations, may be stored in a radiation therapy system controller. Beam station radiation delivery may comprise moving the patient platform to each of the beam stations specified during treatment planning and delivering radiation to the patient target region in accordance with the fluence map for that beam station. The fluence may be delivered by a gantry-mounted therapeutic radiation source (e.g., linac) in a single revolution of the gantry, or may be delivered over multiple gantry revolutions. The number of gantry revolutions per beam station may be determined during treatment planning or may be determined upon segmentation of the fluence map during a treatment session. Alternatively or additionally, the number of arm or gantry arc sweeps may be determined during treatment planning or may be determined upon segmentation of the fluence map. The radiation therapy system may calculate the beamlet sequence to be delivered at each beam station so that the fluence delivered at that beam station matches or approximates the fluence map(s) calculated by the treatment planning system for that beam station. In IMRT, the fluence to be delivered at each beam station may be determined during treatment planning and may be unchanged during the treatment session. The radiation therapy system may calculate the number of revolutions at each beam station to achieve the planned fluence. The radiation therapy system may optionally use multiple passes along IEC-Y (and/or along all beam stations such that each patient region crosses the treatment beam plane multiple times) to deliver the required fluence to reduce the impact of motion on dose delivered to the target. Each "pass" comprises moving the patient platform through all the beam stations determined during treatment planning in one direction (e.g., along the IEC-Y axis), and the successive pass comprises moving the patient platform through all the beam stations in the opposite direction (e.g., in a reverse direction). In BGRT (where the radiation therapy system comprises one or more PET detectors), the number of gantry revolutions at each beam station may be fixed and the radiation therapy system may also use multiple passes along IEC-Y to manage the total delivered fluence at each beam station. Additional passes may be used during a treatment session (i.e., in addition to the passes that were originally specified by the treatment plan) due to patient and/or radiation therapy system variabilities on the day of treatment. For example, a treatment session may include additional passes to deliver fluence that was missed (e.g., residual fluence) due to patient motion and/or radiation therapy system malfunction(s).

In some variations, a prescan image may be acquired at the start of a treatment session. Parameters of the treatment plan may be updated or adjusted based on the prescan data. For example, the treatment plan fluence map may be normalized, and/or the dwell time adjusted, and/or jaw width adjusted per prescan image data. The number of gantry revolutions per beam station may be determined using a PET prescan (or any imaging data, such as MRI, CT, ultrasound, and/or X-ray imaging data) that is acquired prior to the treatment (e.g., on the day of treatment). In the case of BGRT where a PET prescan image is acquired at the start of a treatment session and depending on the PET data (e.g., SUV, localization, etc.), the radiation therapy system may normalize the treatment plan and/or adjust the fluence map for delivery. In some variations, the dwell time (e.g., number of gantry rotations), and/or jaw opening width may optionally be adjusted based on fluence map changes, which may facilitate the delivery of the prescribed dose to the patient target region. For example, a PET prescan image may show increased (or decreased) SUV for a patient target region as compared to treatment planning PET images. This may indicate that more (or less) fluence should be emitted at a particular beam station in order to deliver a prescribed dose to that target region. The controller of the radiation therapy system may widen (or narrow) the jaw opening width to increase (or decrease) fluence emission. Changes in the fluence map may also reflect changes in target region size, so during fluence map segmentation during the treatment session, the number of gantry revolutions may increase (or decrease) if the target region geometry becomes more (or less) complex. In some variations, the number of revolutions per beam station may vary to reduce treatment time. For example, if LOR data acquired at the time of treatment indicates that there is no PET uptake at a beam station that was previously assigned a non-zero fluence emission value, then the dwell time there may be reduced and/or that beam station may be skipped entirely. More generally, moving the patient platform through all the beam stations in multiple passes such that the patient target region(s) cross the treatment beam plane multiple times may provide one or more opportunities to deliver any radiation dose that was missed during a preceding pass.

In some variations, beam station dwell time may be calculated at the start of a treatment session based on the PET prescan. Alternatively or additionally, dwell time may be calculated in real-time, at each beam station, based on detected LORs or imaging data and/or system functions (e.g., if there were any MLC, linac, gantry malfunctions, more time may be spent at a beam station to ensure that intended fluence is delivered). The step distance between beam stations may be modified based on the prescan PET to adjust for any fluence map gradient changes. In some variations, beam station step distance may be calculated at the start of a treatment session based on the prescan PET and/or in real-time using LOR and/or imaging data. In target regions where there is a steep fluence gradient, the distance between beam stations may be less than in target regions where there is a smaller fluence gradient. In some variations, the dwell time for a particular beam station in one patient platform pass may be different from the dwell time for the same beam station in a different pass. For example, in a first pass, the dwell time at a beam station may be a first time duration to deliver a large amount of fluence and in a second (later) pass, the dwell time at that beam station may be a second time duration that is shorter than the first time duration to deliver a lower quantity of fluence (e.g., residuals, possibly resulting from real-time segmentation errors/estimates).

In some variations, the fluence maps for all beam stations may be segmented into machine instructions at the start of a treatment session, while in other variations, the fluence maps may be segmented as the platform is moved to the beam station. In BGRT, because the fluence maps may be updated according to imaging data acquired in real-time (e.g., PET imaging data), segmentation of the updated fluence map for a particular beam station may occur as the platform moves to that beam station. Alternatively or additionally, segmentation of the updated fluence map occur between firing positions as the gantry rotates. In some variations, a fluence map for a beam station may be divided into sub-fluence maps to be delivered over multiple gantry revolutions and/or over sub-firing positions, and the sub-fluence maps may then be segmented into machine instructions for delivery. Before the patient platform is advanced to the next beam station (or moved from the current beam station), the radiation therapy system controller may calculate the radiation delivered at the current beam station and compare that with the fluence map for the beam station to determine whether the desired amount of radiation for that beam station has been delivered. Any fluence difference may be re-delivered as "catch-up" beamlets in additional gantry revolutions at that beam station. For example, the radiation therapy system may track the occurrence of system component failures that result in missed radiation firings, such as magnetron arcs, a "sticky" MLC leaf that did not open (or close) on time, and the like. In some variations, radiation may be delivered over additional gantry revolutions to help compensate for dose instability such that the cumulated delivered dose matches (or better approximates) the planned dose distribution. After the radiation therapy system controller confirms that radiation has been delivered within acceptable tolerances (e.g., as specified/approved by a clinician), the patient platform may then be advanced to the next beam station. Alternatively or additionally, the radiation therapy system controller may evaluate one or more radiation delivery metrics or treatment parameters before deciding whether to move the patient platform from the current beam station to the next beam station. For example, the radiation therapy system controller may move the patient platform to the next beam station based on one or more dose metrics (such as any described above, alone or in combination with multiple dose metrics). In some variations, the patient platform may be moved from one beam station to the next based on a set of instructions (e.g., generated by the treatment plan and/or clinician) that may include the dwell time, and/or jaw opening width, and/or number of revolutions at the particular beam station, and/or radiation pulse parameters (e.g., number, width, duty cycle, energy, MU, etc.) and/or MLC leaf configurations for each therapeutic radiation source firing position. Patient changes and/or any radiation therapy system component errors or failures may alter the dwell time at a beam station from the dwell time estimated at the time of treatment planning. Real-time segmentation allows for radiation delivery that reflects the machine operating state and patient conditions at the time of treatment.

For example, the time a patient platform remains at a beam station during a treatment session may be determined based on the fluence emitted by the therapeutic radiation source and/or radiation therapy system component performance. A method for a radiation delivery system to determine whether to move the patient platform from one beam station to the next beam station (i.e., whether to stop radiation delivery at a beam station and to advance the patient platform to another beam station) may comprise measuring the emitted fluence, comparing the emitted fluence with the fluence map for that beam station as specified during treatment planning (and/or normalized at the start of the treatment session), and calculating a difference between the emitted fluence and the treatment plan fluence map. If the calculated fluence difference is zero and/or below a pre-determined threshold, radiation delivery is stopped and the patient platform is advanced to another beam station. Any fluence difference or fluence residual may be stored in a memory of the radiation therapy system controller. Alternatively or additionally, a method for determining whether to move the patient platform from one beam station may comprise measuring the amount of time the patient platform has been positioned at a beam station, determining whether the time direction exceeds a predetermined threshold (e.g., an upper or maximum threshold), and if that threshold is reached or exceeded, generating an audio, visual and/or tactile notification/alert to the clinician (e.g., the operator of the radiation therapy system). The threshold may be a maximum dwell time, a maximum number of gantry rotations, and/or a maximum quantity of fluence emitted by the linac (e.g., number of MUs). In some variations, when the radiation therapy system has determined that the threshold has been reached or exceeded, the method may comprise generating a visual representation of any fluence difference between the emitted fluence at the beam station and the planned fluence for that beam station. For example, the radiation therapy system may display a graphical representation of the fluence difference to a display monitor or screen, and/or may display numerical values (e.g., metrics) and/or statistics that represent the emitted and/or planned fluence or dose (e.g. MUs emitted vs MUs planned, MUs emitted per gantry rotation, number of gantry rotations, number of linac pulses, etc.). A clinician and/or radiation therapy system operator may review the visual representation and/or fluence metrics or statistics to determine whether to proceed with the radiation treatment session. In some variations, if the emitted fluence exceeds an upper threshold (e.g., a safety boundary) and/or if the emitted fluence or dose profile does not converge to the fluence map for a particular beam station after the patient platform has been positioned at the beam station for a predetermined threshold of time or number of gantry rotations, the radiation therapy system may be configured to stop radiation delivery automatically and to generate a notification to the clinician and/or operator.

Figure 3:
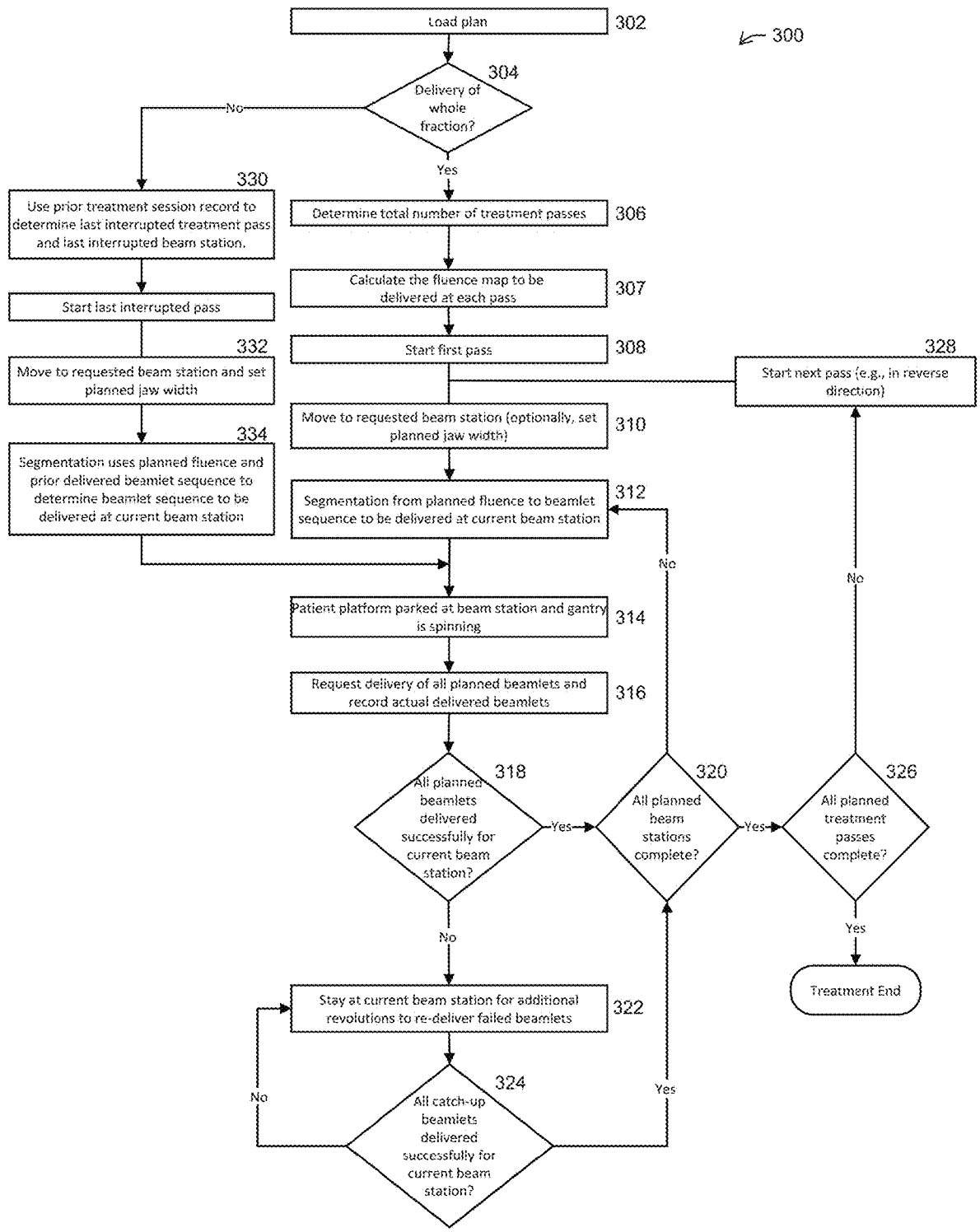
FIG. 3 depicts a flowchart representation of one variation of a method for beam station delivery.

FIG. 3 depicts one variation of a method for beam station radiation delivery. Method (300) may comprise loading (302) fluence map(s) and dose data from a treatment planning system into the memory of the radiation therapy system controller, and determining (304) whether to deliver the entire fraction or dose specified by the fluence maps (e.g., cumulative planned fluence map, and/or fluence maps for all beam stations). If a clinician determines that the entire fraction is to be delivered in the treatment session, method (300) may comprise determining (306) the total number of treatment passes for the treatment session, and starting the first pass (308) by moving (310) the patient platform for the first beam station and optionally setting the desired jaw width. Each pass may be one full scan of a treatment region in one patient platform IEC-Y direction. The method (300) may comprise, before starting the first pass (308), calculating (307) the fluence map to be delivered at each pass. The fluence map to be delivered at each pass may be stored in the radiation treatment system controller. Method (300) may then comprise segmenting (312) the planned fluence map (e.g., the per-pass fluence map) for the first beam station to a beamlet sequence to be delivered at the beam station. The segmented fluence map may comprise specific MLC leaf configurations, number and width of linac pulses at each firing position, etc. In some variations, fluence map segmentation may occur once at the start of delivery at a beam station and/or may occur continuously as the radiation source rotates through the firing positions. For example, some methods may comprise segmenting the fluence map each time the linac arrives at a new firing position (e.g., from about 25 to about 100 times or more per second, about 50 times/second, about 100 times/second), where segmenting the fluence map comprises calculating the fluence that remains to be delivered at the beam station by subtracting the emitted fluence from the planned/prescribed fluence, determining the quantity of fluence deliverable at the new firing position, and segmenting the deliverable quantity of fluence into MLC leaf instructions and/or linac pulse parameters. The patient platform remains stationary (314) at the beam station while the therapeutic radiation source rotates around the platform and delivers radiation according to the segmented fluence map. Method (300) may also comprise recording (316) the actual delivered beamlets, for example, by storing each instance where all system components operated without malfunction. Optionally, the system may record the time of any system component malfunction (e.g., MLC leaf motion delays, MLC compressor constraints, linac misfires, magnetron arcs, external sensor failures, including external gating sensors such as breathing sensors, etc.), the firing position and/or MLC leaf configuration at the time of the component failure, etc. Method (300) may then comprise determining (318) whether all planned beamlets or fluence map(s) have been delivered at the current beam station, and if so, determine (320) whether the planned beamlets or fluence maps have been delivered for all beam stations. Alternatively or additionally, method (300) may comprise determining whether radiation delivery has been carried out according to prescribed dose metrics (e.g., any of the metrics described above) and/or desired treatment parameters (e.g., beam station dwell time, jaw opening width, number of gantry revolutions, therapeutic pulse parameters, MLC leaf configurations) that have been predetermined by the treatment planning system and/or clinician and/or radiation therapy system (e.g., predetermined at an earlier time point in the treatment session). Notably, if no radiation is to be delivered at a beam station, the patient platform may be advanced past that beam station to the next beam station for which a non-zero radiation dose is to be delivered. If the planned beamlets for all beam stations have not yet been delivered, method (300) may comprise moving the platform to the next beam station and repeating (312)-(318). If all delivery to all beam stations have been completed, method (300) may comprise determining (326) whether all passes have been completed. If not, method (300) may then start the next pass (328), which may be in the reverse direction, repeating (312-320) until all passes have been completed. In the event that the controller determines that not all planned beamlets or fluence map(s) have been delivered at the current beam station, i.e., that some beamlets have been missed due to, for example, magnetron arcing and/or any of the machine malfunctions described herein, method (300) may comprise re-delivering (322) the missed beamlets at the current beam station until all such missed or "catch-up" beamlets have been delivered (324). Beamlets may have been missed due to any of the system component malfunctions described above. In some variations, this may extend the dwell time at the beam station beyond what was calculated at treatment planning. Alternatively, this may not extend dwell time, but may alter the fluence emitted during the revolutions and/or firing positions after the radiation therapy system malfunction(s). Once all beamlets have been delivered, the radiation therapy system may proceed to advance the platform to the next beam station or next pass, whichever is applicable.

If the fluence for a pass has been delivered according to the calculated fluence map, the method (300) may comprise calculating the fluence to be delivered at the next pass. In some variations, the fluence to be delivered at each pass may have been calculated at the beginning of the treatment session (e.g., before the first pass at 307) and stored in controller member. Alternatively or additionally, the fluence map for a next pass may be calculated by determining the difference between the cumulative delivered fluence and the cumulative planned fluence, and dividing or partitioning the remaining undelivered fluence over the remaining passes. In some variations, for certain beam stations and/or firing positions, the fluence delivered at each pass may be the same or may be different, depending on the quantization of the fluence map(s) for each beam station. For example, a treatment session may have four passes, and as such, a particular firing position for a particular beam station may be encountered at least four times in the treatment session. If the fluence to be delivered from that firing position for that beam station needs three linac pulses, one pass may be emitted for three of the passes, and no pulse emitted at the fourth pass.

In some variations, a treatment session may be a supplemental or "make-up" treatment session to deliver dose that was missed at a previous, interrupted treatment session. In such case, it may be determined (304) that the entire fraction need not be delivered, but may instead continue delivery from the point where the previous session stopped. Method (300) may then comprise determining (330) the last interrupted beam station and pass based on the records from the previous treatment session. The radiation therapy system may move (332) the platform to the last interrupted beam station and segment (334) the fluence map for that beam station (especially if any system parameters have changed since the last treatment session) and continue delivery of radiation as per (312)-(328). Segmentation (334) may comprise generating a set of MLC leaf configurations or patterns, number of pulses and pulse with for each firing position from the fluence map for a beam station. In some variations, the fluence map may have been updated and/or normalized using any new and/or updated imaging or prescan data. As described above, the radiation therapy system constantly tracks and records the time of any system component malfunction (e.g., MLC leaf motion delays, MLC compressor constraints, linac misfires, magnetron arcs, external sensor failures, including external gating sensors such as breathing sensors, etc.), the firing position and/or MLC leaf configuration at the time of the component failure, etc., which may be used later in the same or different treatment session for resuming dose delivery (i.e., of a partial fraction). Since such data is recorded, treatment can resume from the same beam station when the interruption occurred (though not necessarily at the same firing angle). This may be more precise than resuming delivery in helical delivery where the patient platform is constantly moving during radiation delivery, since the synchronization of platform motion (which may include platform location and speed) and gantry rotation at the time of the interruption can be difficult to precisely replicate at a later time point.

A treatment session may be interrupted due to one or more components of a radiation therapy system malfunctioning, one or more patient-specific factors, and/or based upon clinician and/or operator instructions. Examples of component malfunctions that may trigger a session interruption may include, but are not limited to, "sticky" MLC leaves that are sluggish and/or cannot move due to insufficient motive force and/or other failures, magnetron arcing, gantry rotation errors, loss of synchronization between the patient platform and/or the therapeutic radiation source position and/or gantry rotation and/or MLC operation, etc. Examples of patient factors that may trigger a session interruption may include, but are not limited to, discomfort, inability to remain still, declining physical or mental conditions, poor and/or non-specific PET tracer uptake, etc. A clinician and/or operator may pause or end a treatment session for a variety of reasons, for example, if they determine that the treatment plan is not suited for delivery at the time of the treatment session, and/or if the delivered fluence appears to deviate from the fluence specified by the treatment plan, and/or any patient-safety concerns or issues, and/or any medically-relevant concerns or issues, etc. In some variations, a radiation therapy system may comprise a system shut-down mechanism that automatically halts the emission of radiation from the therapeutic radiation source and/or closes the MLC leaves and/or closes the jaws when activated by the patient and/or operator. For example, the shut-down mechanism may comprise a button, lever, switch, or any other mechanical trigger that is accessible to a patient positioned on the platform. Alternatively or additionally, the shut-down mechanism may comprise a button, lever, switch or any other mechanical trigger that is accessible to a clinician and/or operator. When the shut-down mechanism has been activated, a signal may be transmitted to the therapeutic radiation source to halt the emission of radiation, and the system configuration data at the time the shut-down mechanism was activated is stored in system controller memory. Examples of system configuration data that may be stored when a treatment session has been interrupted may comprise beam station data (e.g., current beam station data, which beam stations have already been visited, beam stations not yet visited, etc.), gantry rotation configuration or revolutions, dwell time at the beam station at the time of the session interruption, firing position (or firing angle) index, MLC configuration, patient platform pass index, etc. The cumulative fluence delivered during the treatment session up until the interruption and/or the fluence delivered at the present beam station up until the interruption may be stored in system controller memory. The system configuration data may be used for resuming therapy at a later time.

In some variations, the treatment session may be resumed without a new patient setup and registration (i.e., the patient remains on the platform after the interrupt and radiation delivery resumes on the same session or day) while in other variations, the treatment session may be resumed after a new patient set up and registration (i.e., the patient is removed from the platform after the interrupt and radiation delivery resumes at a later time or on a different day). In variations where radiation delivery is based on PET emissions (e.g., LORs) and/or imaging data acquired at the time of treatment (e.g., as in BGRT), resuming a treatment session at a different time may comprise obtaining a PET prescan, normalizing the treatment plan using the PET prescan data, moving the patient platform to the beam station where the previous treatment session was interrupted, positioning the therapeutic radiation source at the firing position where the previous session was interrupted, and delivering radiation according to the treatment plan that has been normalized to the updated PET prescan. Additional details regarding treatment plan normalization based on real-time acquired imaging data may be found in U.S. patent application Ser. No. 16/138,631, filed Sep. 21, 2018, which is hereby incorporated by reference in its entirety. Alternatively or additionally, an interrupted treatment session may be resumed at a later time by moving the patient platform to the beam station where the previous treatment session was interrupted, positioning the therapeutic radiation source at the firing position where the previous session was interrupted, and delivering radiation according to the treatment plan (i.e., without normalizing the treatment plan based on real-time acquired imaging data). For example, in IMRT treatment plans where radiation delivery is based on a sequence of x control points $cp_{(1 \ldots x)}$ which specify, for example, segmented fluence maps for each beam station, firing position, and/or pass in a treatment session, resuming an interrupted treatment session (where the interrupt occurred at control point $cp_{interrupt}$) may comprise setting up and registering the patient according to the setup and registration in the interrupted treatment session, moving the patient platform to the control point where the interrupt occurred $cp_{interrupt}$ (i.e., moving the patient platform to the beam station of the control point) and delivering therapeutic radiation according to the next control point $cp_{(interrupt+1)}$, and so forth until radiation has been delivered to the patient in accordance with all of the treatment plan control points (e.g., from $cp_{(interrupt+1)} \ldots cp_{(x-2)}$, $cp_{(x-1)}$, $cp_x$). Delivering radiation to the patient target regions only when the patient platform is stopped at a beam station may help the radiation therapy system to more precisely resume radiation delivery after an interruption and to even resume radiation delivery in the same session, shortly after the interrupt has occurred. In a helical delivery system where the patient platform is continuously moving as radiation is delivered (e.g., where radiation is delivered from a therapeutic radiation source that may be continuously moving), it may be challenging to precisely record the location of the patient platform and the location of the therapeutic radiation source (e.g., firing position or angle) at the time of the interruption, since the platform may have moved after the interruption, and/or the positional and/or temporal synchronization between the patient platform and the therapeutic radiation source (and optionally, the MLC associated with the therapeutic radiation source) may challenging to ascertain or maintain. For example, a treatment session may be interrupted due to a MLC leaf failure. In beam station delivery, the radiation therapy system may be configured to determine the fluence that was supposed to be delivered using the defective MLC leaf, and segment the fluence that was not delivered (due to the defective leaf) to be delivered at an alternate firing position and/or using other MLC leaves. Since the patient platform has not moved from the beam station where the interrupt occurred, the missing fluence may be delivered during the same session and treatment may resume. Or, if the magnetron arcs, the radiation therapy system may keep the patient platform at a beam station to wait until the magnetron is stable and to attempt re-delivery. However, in helical delivery systems where the patient platform is in constant motion, fluence that was not delivered due to an MLC leaf error may be difficult to deliver in the same session since by the time the leaf error is detected and the fluence re-segmented, the platform would have changed its location. If the magnetron arcs during radiation delivery, it can be difficult for a helical radiation therapy system to deliver the missed fluence, since the platform would have changed its position by the time the magnetron has stabilized.

As described previously, the jaw opening width may be varied at each beam station. Varying the jaw opening width may help to facilitate control of the IEC-Y dose or fluence gradient. For example, smaller jaw widths, such as about 1 cm or less, can be used when higher IEC-Y dose or fluence gradients are desired, and larger jaw widths, such as greater than about 2 cm, can be used to deliver dose in a lower IEC-Y dose or fluence gradients. In some variations, enlarging the jaw opening width may cause the irradiation field at one beam station to overlap with the irradiation field at one or more adjacent beam stations. In situations where a relatively low dose gradient or fluence gradient is prescribed (e.g., for tumors larger than about 4 cm in the IEC-Y dimension), or in situations where the prescribed dose to a patient region is zero, non-overlapping irradiation fields between beam stations may be desirable, as this may help increase delivery efficiency and reduce treatment time. During beam station delivery (for either IMRT or BGRT), the fluence in the axial plane (XZ) may be modulated by setting a jaw opening width that creates irradiation fields that overlap with adjacent beam stations and by performing multiple revolutions per beam stations, where each revolution has a different MLC leaf configuration for each firing position. For a beam station where a higher level of dose or fluence modulation is desired, radiation may be delivered over more revolutions as compared with a beam station where a lower level of dose or fluence modulation is desired. In some variations, there may not be any dose or fluence modulation across the beam stations, e.g., an unmodulated treatment mode, where the modulation factor is 1. In this case, the MLC leaf configuration for one or more firing positions does not change over the multiple revolutions and may not generate a variable intensity pattern for each firing position in the axial plane, but may instead be used to shape the aperture of the beam around the tumor dimensions at each firing position. For example, for each firing position the beam aperture can be defined by the width of leaf opening in the X-direction and by the width of jaw opening in the IEC-Y direction that conforms to a patient target region boundary (e.g., a PTV boundary) in a beam's eye view at each firing position. That is, the radiation therapy system may perform 3D conformal delivery while the platform remains stationary at a beam station. Unmodulated delivery may help to reduce treatment time and also help to reduce the complexity and computational intensity of treatment planning, since the optimization is done only on the beam station dwell time and jaw widths (not MLC leaf configuration). In some variations, beam station radiation delivery may comprise holding the therapeutic radiation source at a particular (e.g., first) firing position while the patient platform is moved to each of the beam stations specified during treatment planning. While the platform is held stationary at the beam station, the radiation beamlet defined by the MLC leaf configuration for that (e.g., first) firing position and beam station may be delivered. The MLC leaf configuration may change for each beam station, as specified by the fluence map. After the patient platform has been positioned at each beam station (e.g., from beam stations 1, 2, 3, . . . N) and the specified radiation beamlets have been delivered from the particular (e.g., first) firing position, the gantry may move the therapeutic radiation source to the next (e.g., second) firing position and the patient platform may be moved through each of the beam stations, where the MLC leaf configuration is adjusted for that firing position at each beam station. In some variations, for the next (e.g., second) firing position, the patient platform may be moved to each beam station in reverse order (e.g., from beam stations N, N–1, N–2, . . . , 1), where the direction of patient platform motion alternates as the therapeutic radiation source changes its firing position. Alternatively or additionally, the therapeutic radiation source may be held at a single firing position while the patient platform moves across all the beam stations twice, i.e., two passes where the first pass is from beam station 1, 2, . . . N–1, N, and the second pass is from beam station N, N–1, . . . 2, 1. The number and direction of passes for each firing position may vary, depending on whether the desired or prescribed dose has been delivered according to the dose objectives.

Figure 4:
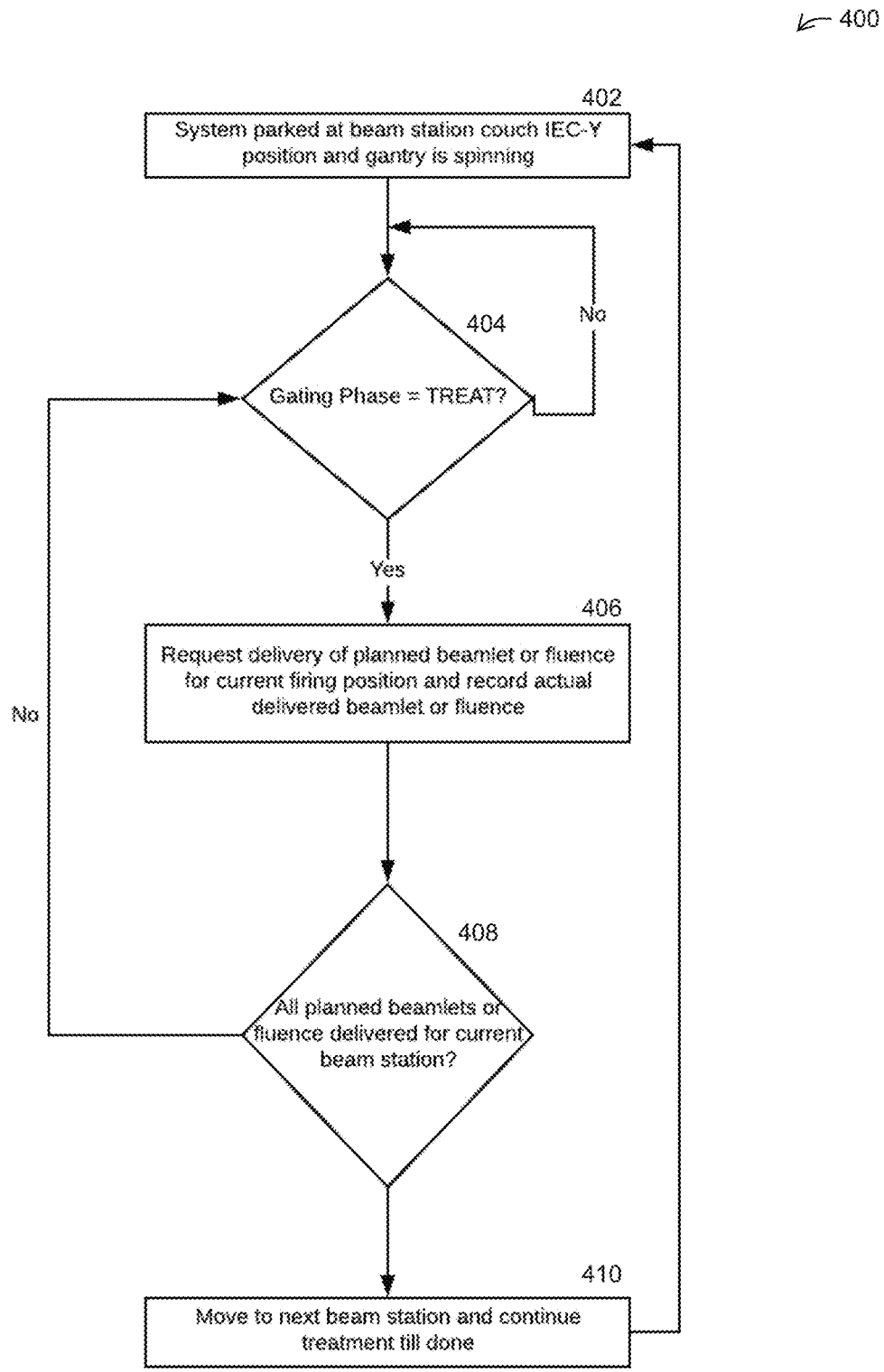
FIG. 4 depicts a flowchart representation of one variation of a method for gated beam station radiation delivery.

Beam station radiation delivery may also be used to facilitate gated radiation delivery, where the emission of therapeutic radiation beams are timed based on motion of the target regions and/or patient. In some variations, real-time acquired imaging data and/or images (e.g., PET imaging data) may be used to identify the changing position of the target region and/or patient while the patient platform is positioned (i.e., stationary) at a given beam station. The radiation therapy system can "wait" for the target region to move to a predetermined (e.g., during treatment planning) treatment location range before radiation is applied. This type of delivery is not possible with helical delivery, because the patient platform is constantly moving while the target region is also moving, and the relative motion between the platform and target region can be difficult to trigger on for radiation delivery. One variation of a method of gated beam station radiation delivery is depicted in FIG. 4. Method (400) may comprise moving (402) the patient platform to a beam station, and stopping at the beam station while the therapeutic radiation source is continuously rotating around the platform and determining (404), based on target position and/or motion data calculated from real-time acquired imaging data, whether the target region is located in a predetermined treatment location or is in a phase where treatment is indicated. If it is determined that the target region is not located in the predetermined treatment location and/or the motion of the target region is in a phase where treatment is not indicated, no radiation is delivered, and the platform remains at the beam station (402). If it is determined that the target region not located in the predetermined treatment location and/or the motion of the target region is in a phase where treatment is indicated, method (400) may comprise delivering (406) the planned beamlet or fluence for the current firing position and recording in the system controller memory that a beamlet or fluence was delivered. This may be repeated (408) until all the beamlets or fluence for that beam station have been delivered (see also FIG. 3), after which the patient platform may be moved (410) to next beam station. Method (400) may be repeated, until all beamlets or fluence for all beam stations have been delivered.

While various inventive variations have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive variations described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive variations described herein. It is, therefore, to be understood that the foregoing variations are presented by way of example only and that, within the scope of the appended claims and equivalents thereto, inventive variations may be practiced otherwise than as specifically described and claimed. Inventive variations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The invention claimed is:

1. A method for converting a treatment plan for helical delivery to a treatment plan for beam station delivery, the method comprising:
   discretizing a planned fluence map of a helical treatment plan into fluence maps for a plurality of sample points along a longitudinal axis of patient platform motion;
   mapping each sample point to a beam station of a set of beam stations;
   assigning the fluence map of each sample point to its mapped beam station; and
   generating a beam station fluence map for each beam station by combining the fluence maps of the sample points that have been assigned to the beam station.

2. The method of claim 1, wherein the sample points are patient platform positions along an IEC-Y axis.

3. The method of claim 1, further comprising calculating a radiation dose to be delivered to a target region by combining the beam station fluence maps over the beam stations in the set of beam stations.

4. The method of claim 3, further comprising comparing the calculated radiation dose with a prescribed radiation dose to determine a dose difference between the calculated radiation dose and the prescribed radiation dose to the target region.

5. The method of claim 4, further comprising adjusting a beam station fluence map by an adjustment factor based on the dose difference.

6. The method of claim 1, wherein discretizing the planned fluence map of the helical treatment plan comprises sectioning the planned fluence map into helical segments along the longitudinal axis.

7. The method of claim 6, wherein a spacing between the plurality of sample points is a width of the helical segments.

8. The method of claim 7, wherein mapping each sample point to a beam station comprises mapping one or more helical segments to a beam station.

9. The method of claim 8, wherein a helical segment is mapped to a beam station based on a location of the helical segment on the longitudinal axis.

10. The method of claim 1, wherein a spacing between the plurality of sample points is selected based on characteristics of the helical treatment plan.

11. The method of claim 1, wherein a spacing between the plurality of sample points is the same as a spacing between beam stations in the set of beam stations.

12. The method of claim 1, wherein multiple sample points map to a single beam station.

13. The method of claim 1, wherein a sample point is mapped to a beam station based on a location of the sample point on the longitudinal axis.

14. The method of claim 1, further comprising segmenting the beam station fluence map into instructions for a therapeutic radiation source and a multi-leaf collimator disposed in a beam path of the therapeutic radiation source.

15. The method of claim 1, further comprising transmitting the generated beam station fluence maps to a radiation therapy system.

16. The method of claim 15, further comprising segmenting the beam station fluence map into instructions for a therapeutic radiation source and a multi-leaf collimator disposed in a beam path of the therapeutic radiation source during a treatment session.

17. The method of claim 1, further comprising adjusting the beam station fluence maps using imaging data acquired during a treatment session.

18. A radiation therapy system comprising:
a gantry rotatable about a longitudinal axis;
a therapeutic radiation source mounted on the gantry and configured to emit radiation according to a fluence map;
a patient platform movable to a plurality of beam stations at predetermined locations; and
a controller in communication with the gantry, the therapeutic radiation source, and the patient platform, the controller configured to discretize a planned fluence map of a helical treatment plan into fluence maps for a plurality of sample points along the longitudinal axis, map each sample point to a beam station, assign the fluence map of each sample point to its mapped beam station, and a generate beam station fluence map for each beam station by combining the fluence maps of the sample points that have been assigned to the beam station.

19. The system of claim 18, wherein the controller is further configured to calculate a radiation dose to be delivered to a target region by combining the beam station fluence maps of the plurality of beam stations, and to compare the calculated radiation dose with a prescribed radiation dose to determine a dose difference between the calculated radiation dose and the prescribed radiation dose to the target region.

20. The system of claim 19, wherein the controller is configured to adjust a beam station fluence map based on the determined dose difference.

21. The system of claim 18, wherein the radiation therapy system comprises an imaging system, and the controller is configured to adjust a beam station fluence map using imaging data acquired by the imaging system.

22. The system of claim 18, wherein the controller is configured to segment the beam station fluence map into instructions for the therapeutic radiation source and a multi-leaf collimator disposed in a beam path of the therapeutic radiation source.

23. The system of claim 18, wherein the predetermined locations are locations along the longitudinal axis.

* * * * *